(12) United States Patent
O'Donnell et al.

(10) Patent No.: US 11,679,219 B2
(45) Date of Patent: Jun. 20, 2023

(54) PATIENT INTERFACE AND HEADGEAR FOR A RESPIRATORY APPARATUS

(71) Applicant: Fisher & Paykel Healthcare Limited, Auckland (NZ)

(72) Inventors: Kevin Peter O'Donnell, Auckland (NZ); Samuel Robertson Frame, Auckland (NZ); Martin Paul Friedrich Kramer, Auckland (NZ); Sean Joel Babbage, Auckland (NZ); Peter Geoffrey Hawkins, Auckland (NZ); Milanjot Singh Assi, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 942 days.

(21) Appl. No.: 16/519,567

(22) Filed: Jul. 23, 2019

(65) Prior Publication Data
US 2019/0344036 A1 Nov. 14, 2019

Related U.S. Application Data

(63) Continuation of application No. 14/888,685, filed as application No. PCT/NZ2014/000082 on May 7, 2014, now Pat. No. 10,406,311.
(Continued)

(51) Int. Cl.
*A61M 16/00* (2006.01)
*A61M 16/06* (2006.01)
*A61M 16/08* (2006.01)

(52) U.S. Cl.
CPC .... *A61M 16/0666* (2013.01); *A61M 16/0672* (2014.02); *A61M 16/0683* (2013.01);
(Continued)

(58) Field of Classification Search
CPC .......... A61M 16/0666; A61M 16/0672; A61M 16/0683; A61M 16/0816; A61M 16/0875; A61M 2209/082
See application file for complete search history.

(56) References Cited

U.S. PATENT DOCUMENTS 3,513,844 A 5/1970 Smith
3,682,171 A 8/1972 Dali et al.
(Continued)

FOREIGN PATENT DOCUMENTS

AU 2014263285 11/2014
AU 2019202375 5/2019
(Continued)

OTHER PUBLICATIONS

Office Action for JP Patent Application No. 2019-065642 dated Jan. 18, 2021; 2 pages.
(Continued)

*Primary Examiner* — Steven O Douglas
(74) *Attorney, Agent, or Firm* — Knobbe, Martens, Olson & Bear, LLP

(57) ABSTRACT

This invention relates to headgear and a patient interface, or components of a headgear or patient interface, such as a nasal cannula. In one embodiment is a size adjustable headstrap to be provided as a headgear or a part thereof, in another is a portion of a headstrap or component for association therewith in which the portion or component facilitates improved location of the strap upon a user's face, in another embodiment is a system for encapsulating or covering a connector from contact with a user's face or facial skin, in another embodiment is a face mount part or body for a patient interface of a particular configuration, and in yet a further embodiment is a gases flow manifold for delivering
(Continued)

of gases to a patient interface of a particular configuration for improved patient comfort.

57 Claims, 13 Drawing Sheets

Related U.S. Application Data

(60) Provisional application No. 61/918,624, filed on Dec. 19, 2013, provisional application No. 61/895,942, filed on Oct. 25, 2013, provisional application No. 61/820,564, filed on May 7, 2013.

(52) U.S. Cl.
CPC ..... *A61M 16/0816* (2013.01); *A61M 16/0875* (2013.01); *A61M 2209/082* (2013.01)

(56) References Cited

U.S. PATENT DOCUMENTS

| | | |
|---|---|---|
| 3,754,552 A | 8/1973 | King |
| 4,454,880 A | 6/1984 | Muto et al. |
| 5,335,656 A | 8/1994 | Nowe et al. |
| 6,119,694 A | 9/2000 | Correa et al. |
| D533,269 S | 12/2006 | McAuley et al. |
| 7,178,525 B2 | 2/2007 | Matula et al. |
| 7,231,921 B2 | 6/2007 | Palmer |
| D551,340 S | 9/2007 | Wood et al. |
| D556,900 S | 12/2007 | Guney et al. |
| D559,383 S | 1/2008 | Nalagatla et al. |
| D566,835 S | 4/2008 | Andrews et al. |
| D586,258 S | 2/2009 | Guney et al. |
| D586,911 S | 2/2009 | McAuley et al. |
| 7,493,902 B2 | 2/2009 | White et al. |
| 7,559,327 B2 | 7/2009 | Hernandez |
| D610,901 S | 3/2010 | Jones |
| D614,290 S | 4/2010 | Judson et al. |
| D627,059 S | 11/2010 | Wood et al. |
| 7,900,628 B2 | 3/2011 | Matula et al. |
| D637,285 S | 5/2011 | Bradley et al. |
| 7,987,850 B2 | 8/2011 | Zollinger et al. |
| D650,741 S | 12/2011 | Sun et al. |
| D661,796 S | 6/2012 | Andrews et al. |
| D662,200 S | 6/2012 | Eghbal et al. |
| D664,496 S | 7/2012 | Cohen |
| D665,496 S | 8/2012 | Lee |
| 8,267,092 B2 | 9/2012 | White et al. |
| 8,333,194 B2 | 12/2012 | Lewis et al. |
| D679,809 S | 4/2013 | Clarke et al. |
| D681,440 S | 5/2013 | Yu |
| 8,475,369 B2 | 7/2013 | Boatner et al. |
| 8,522,782 B2 | 9/2013 | Lewis et al. |
| D692,554 S | 10/2013 | Siew et al. |
| 8,573,219 B2 | 11/2013 | Wondka |
| 8,616,203 B2 | 12/2013 | Jaffe et al. |
| D703,464 S | 4/2014 | Koch |
| 8,839,791 B2 | 9/2014 | Allum et al. |
| 8,851,076 B2 | 10/2014 | White et al. |
| 8,887,725 B2 | 11/2014 | Hernandez et al. |
| D723,363 S | 3/2015 | Symons |
| D723,679 S | 3/2015 | Neff et al. |
| D724,720 S | 3/2015 | O'Connor et al. |
| D739,223 S | 9/2015 | Paik et al. |
| D745,141 S | 12/2015 | Hung |
| D747,792 S | 1/2016 | Babbage et al. |
| D766,711 S | 9/2016 | Babbage |
| D796,027 S | 8/2017 | Babbage et al. |
| D797,921 S | 9/2017 | Huang et al. |
| 9,849,262 B2 | 12/2017 | White et al. |
| 9,907,925 B2 | 3/2018 | McAuley et al. |
| D825,053 S | 8/2018 | Ronayne et al. |
| D849,243 S | 5/2019 | Wilson et al. |
| D859,646 S | 9/2019 | Scampoli et al. |
| 10,406,311 B2 | 9/2019 | O'Donnell et al. |
| D881,382 S | 4/2020 | Chang |
| 2002/0096176 A1 | 7/2002 | Gunaratnam et al. |
| 2004/0244804 A1 | 12/2004 | Olsen et al. |
| 2004/0261797 A1 | 12/2004 | White et al. |
| 2005/0002882 A1 | 1/2005 | Amari et al. |
| 2005/0028822 A1 | 2/2005 | Sleeper et al. |
| 2006/0231103 A1 | 10/2006 | Matula, Jr. et al. |
| 2007/0186931 A1 | 8/2007 | Zollinger et al. |
| 2008/0099024 A1 | 5/2008 | Gunaratnam et al. |
| 2009/0044808 A1 | 2/2009 | Guney et al. |
| 2010/0108073 A1 | 5/2010 | Zollinger et al. |
| 2010/0192957 A1 | 8/2010 | Hobson et al. |
| 2010/0258136 A1 | 10/2010 | Doherty et al. |
| 2011/0067704 A1 | 3/2011 | Kooij et al. |
| 2011/0146685 A1 | 6/2011 | Allan et al. |
| 2011/0271962 A1 | 11/2011 | White et al. |
| 2012/0067349 A1 | 3/2012 | Barlow et al. |
| 2012/0204870 A1 | 8/2012 | McAuley et al. |
| 2012/0304999 A1 | 12/2012 | Swift et al. |
| 2012/0318270 A1 | 12/2012 | McAuley et al. |
| 2013/0008447 A1 | 1/2013 | Gunaratnam et al. |
| 2013/0008449 A1 | 1/2013 | Busch et al. |
| 2013/0263859 A1* | 10/2013 | Ho .................. A61M 16/0683 128/206.21 |
| 2016/0015296 A1 | 1/2016 | Garaycochea |
| 2019/0262574 A1 | 8/2019 | Sweeney et al. |
| 2019/0298961 A1 | 10/2019 | Hsiung et al. |
| 2019/0344036 A1 | 11/2019 | O'Donnell et al. |

FOREIGN PATENT DOCUMENTS

| | | |
|---|---|---|
| AU | 2021202249 | 5/2021 |
| CN | 1750854 | 3/2006 |
| EP | 2994181 | 3/2016 |
| EP | 3626294 | 3/2020 |
| GB | 1342932 | 1/1974 |
| GB | 2176832 | 1/1987 |
| GB | 2465689 | 6/2010 |
| GB | 2531173 | 4/2016 |
| GB | 2580001 | 7/2020 |
| GB | 2584781 | 12/2020 |
| JP | 2005-040589 | 2/2005 |
| JP | 2006-518231 | 8/2006 |
| JP | 2006-528231 | 12/2006 |
| JP | 2009-039528 | 2/2009 |
| JP | 2010-131400 | 6/2010 |
| NZ | 724289 | 2/2019 |
| WO | WO 2007/114492 | 10/2007 |
| WO | WO 2009/099995 | 8/2009 |
| WO | WO 2011/062510 | 11/2010 |
| WO | WO 2012/053910 | 4/2012 |
| WO | WO 2012/077036 | 6/2012 |
| WO | WO 2012/085755 | 6/2012 |
| WO | WO 2013/022356 | 2/2013 |
| WO | WO 2014/015382 | 1/2014 |
| WO | WO 2014/142681 | 9/2014 |
| WO | WO 2014/182179 | 11/2014 |

OTHER PUBLICATIONS

International Search Report; PCT/NZ2014/000082; dated Nov. 20, 2014; 10 pages.
Extended European Search Report; PCT/NZ2014/000082; dated Nov. 8, 2016; 14 pages.
Chinese Examination Report, dated Mar. 23, 2018, 13 pages.
Japanese Examination Report; dated Apr. 2, 2018, 8 pages.
Australian Examination Report, dated Apr. 3, 2018, 4 pages.
Chinese Examination Report; dated May 15, 2018; 10 pages.
European Examination Report; dated May 24, 2018; 5 pages.
Chinese Examination Report; dated Nov. 20, 2018; 21 pages.
Japanese Examination Report; dated Nov. 29, 2018; 4 pages.
GB Examination Report; dated Jun. 21, 2019; 6 pages.
Taiwan Examination Report; dated Aug. 2, 2019, 1 page.
Board Opinion for CN Application No. 201480034448.3 dated Aug. 26, 2020; 7 pages.
Examination Report for GB Application No. 2004848.4 dated Aug. 10, 2020; 3 pages.

(56) References Cited

OTHER PUBLICATIONS

Office Action for TW Application No. 103116253 dated Jul. 6, 2020; 9 pages.
Examination Report for Application No. 3987/KOLNP/2015 dated Nov. 3, 2020; 5 pages.
Examination Report for Application No. AU 2019202375 dated Mar. 11, 2020; 4 pages.
Examination Report for Japanese Application No. 2019-065642; 2 pages.
Examination Report for CA Application No. 2,911,413 dated Dec. 24, 2020; 6 pages.
Examination Report for Application No. GB2004846.8 dated Jun. 12, 2020; 2 pages.
Examination Report for Application No. CA2911413 dated Jun. 15, 2020; 4 pages.
Extended European Search Report for Application No. 19205706.5 dated Feb. 2, 2020; 17 pages.
Examination report for GB Application No. GB 2004846.8 dated Apr. 17, 2020; 6 pages.
Examination Report for Application No. GB2004846.8 dated Jul. 14, 2020; 3 pages.
Exam Report for CA Application No. 2,911,413, dated Oct. 12, 2021, 5 pages.

* cited by examiner

PATIENT INTERFACE AND HEADGEAR FOR A RESPIRATORY APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The invention relates particularly, though not solely, to the delivery of humidified gases to a patient in need of respiratory assistance by way of a patient interface, such as a nasal cannula, and a headgear for supporting or retaining of a patient interface, such as nasal cannula, upon a user.

BACKGROUND OF THE INVENTION

It is important in the design of a respiratory assistance system to provide a patient interface and headgear that are comfortable to the user, easy to wear and that retain their operational position upon movement of the user during use.

Providing for alternative patient interface and headgear systems allows for users to choose the style or type of equipment to use. Such selection may be made upon comfort, or better suited retention of the patient interface upon a user for improved respiratory therapy delivery, or both of these. For example, alternative retention configurations or setups may be provided by different headgear for different patient interfaces.

Nasal cannula can be used to supply high flow therapies. In some situations, paediatric patients use high flow therapy. There is a gap in the market for a nasal high flow cannula (especially for the 2-12 years age group) capable of delivering high flow and high humidity and comfortable enough to wear overnight and able to be fastened on the face of a young child.

It is therefore an object of the present invention to provide a patient interface or a headgear or both, designed to go at least some way toward achieving some or all of the above considerations or to at least provide the public with a useful choice.

SUMMARY OF THE INVENTION

The present invention generally relates to paediatric nasal cannula. More particularly, certain features, aspects and advantages of the present invention relates to such cannula designed for high flow application.

In some configurations, a low resistance to flow cannula can be used to deliver nasal high flow over a wide flow range (e.g., 10-50 L/min), particularly for children 2-12 years old. The paediatric cannula advantageously can be used in the home and in the hospital.

In some such configurations, the paediatric cannula allows the wide flow range to be used with low delivery pressures.

In some configurations, the paediatric cannula can be used in combination with one or more structures to secure the paediatric cannula to the patient. For example, in some such configurations, the paediatric cannula can be used in combination with one or more of a strap and an adhesive patch assembly. In such configurations, the strap and the adhesive patch assembly can be used together or in the alternative.

In a first aspect the invention may broadly be said to involve a strap as part of a headgear for a patient interface comprising:

a strap, the strap having a pair of primary end portions, each of the primary end portions to be connected to a patient interface or to a component which is to be connected to the patient interface, and intermediate of each primary end portion is a pair of secondary end portions releasably connectable with each other to establish a continuous strap between the primary end portions of a starting length, the continuous strap for assisting in the retention of a patient interface upon a patient, and wherein each secondary end portion is adapted to be releasably connectable with a respective end portion of an additional strap segment to establish a continuous strap between the primary end portions of an extended strap length relative to the starting length.

Preferably each end portion of the additional strap segment comprises a connector coupled to the strap segment and each secondary end portion of the strap comprises a connector coupled to the strap.

Preferably the connector of each strap segment is configured to couple the connector the connector of the respective secondary end portion of the strap.

Preferably the connector of each secondary end portion of the strap is configured to couple the connector of the other secondary end portion of the strap and the connector of at least one end portion of the additional strap segment.

Preferably the connector of each of the end portion of the additional strap segment or the connector of each secondary end portion of the strap, or both, is of or comprises: male or female parts or both, for receipt by and connection to complementary male or female parts of another respective connector, and friction fit parts for retaining connection between the respective connectors.

Preferably the connector comprises a projecting male part for receipt by a recessed female part of a respective connector and a recessed female part for receipt of a projecting male part of the respective connector.

Preferably the connector is capable of receiving and retaining a respective terminal end of the associated strap or associated additional strap segment.

Preferably the connector is configured to retain the respective terminal end by a friction fit engagement.

Preferably the connector comprises a series of internal teeth located upon a body of the connector for establishing a friction fit engagement with the respective terminal end, and a jaw of the body of the connector configured to close upon the teeth to securely retain the terminal end of the associated strap or associated additional strap segment upon the teeth.

Preferably the strap is of an elastic, textile material.

Preferably the additional strap segment is of an elastic, textile material.

Preferably the additional strap segment comprises one or more additional strap segments releasably connectable to one another in an end to end relationship to formed a single continuous additional strap segment for releasably connecting to the secondary end portions of the strap.

The additional strap segment may be of any combination of one or more of the following lengths: about 2 cm, about 4 cm, or about 6 cm.

In a second aspect the invention may broadly be said to involve a headgear for a patient interface comprising a strap forming a part of the headgear for assisting in retaining or stabilising of a patient interface upon a user, wherein the strap, or a section of the strap, to be located upon or to be placed in contact with the face or a portion of a user's face includes a surface region for frictionally engaging with the user's face, the surface region being of a relatively higher frictional surface material than the remainder of the strap forming the or a part of the headgear.

Preferably the strap or a respective section of the strap, includes two symmetric surface regions for frictionally engaging with two symmetric portions on either side of the user's face.

Preferably a remainder of the strap is arranged to extend as a non-facial contacting strap or section of strap which is to extend beyond the user's face or the portion of the user's face.

Preferably each surface region for frictionally engaging with the user's face or a portion of the user's face including the relatively higher frictional surface material assists with retaining or stabilising of a patient interface upon the face of a user.

Preferably each surface region comprises a material applied to the strap or the respective section of strap.

In a first embodiment the material applied is in the form of a sleeve positioned about the strap or the respective section of strap.

Preferably the sleeve is configured to removeably couple about the strap or the section of the strap.

Preferably the strap or the respective section of the strap extends through a passage in the sleeve.

Preferably the strap or the respective section of the strap is adapted to be threaded through the passage.

In an alternative embodiment the material applied is in the form of a material coated upon the strap or the respective section of strap.

In yet another alternative embodiment the material applied is over-moulded upon the strap or the respective section of strap.

Preferably in any embodiment the material applied is smooth and comfortable for skin contact.

Preferably the material applied is a Thermoplastic Elastomer.

Preferably each surface region is a surface of wider surface area at an end to be located more adjacent to the patient interface than the surface area of an opposing end more distant from the patient interface.

Preferably surface region tapers from the relatively wider surface area to the relatively lesser surface area.

Preferably the strap or each section of the strap including the surface region further comprises a component of the strap configured to releasably couple the patient interface.

Preferably each portion of the user's face includes a cheek of the user.

In a third aspect the invention may broadly be said to involve a headgear for a patient interface comprising a strap forming a part of the headgear for assisting in retaining or stabilising of a patient interface upon a user, a first connector at a first end portion of the strap for connecting the strap to the patient interface, and a first cheek engaging member adapted to encapsulate the first connector and having a surface region adapted to locate between the user's cheek and the connector to minimise direct contact of the connector with the user's skin in use.

Preferably the headgear further comprises a second connector at a second opposing end portion of the strap for connecting the strap to the patient interface, and a second cheek engaging member configured to encapsulate the second connector and having a surface region adapted to locate between the user's other cheek to minimise direct contact of the connector with the user's skin in use.

Preferably each cheek engaging member is configured to removeably couple about the respective connector.

Preferably the surface region of each cheek engaging member comprises a material that is substantially softer than a material of the respective connector.

Preferably the surface region of each cheek engaging member comprises of a relatively higher frictional surface material than the respective connector to assist with retaining or stabilising of a patient interface upon the face of a user.

Preferably the material is a Thermoplastic Elastomer.

Preferably the surface region of each cheek engaging member is a surface of wider surface area at an end of the respective cheek engaging member more adjacent to the patient interface than a surface area of an opposing end of the cheek member more distant from the patient interface.

Preferably the surface region of each cheek engaging members tapers from a relatively wider end to a relatively lesser end.

Preferably each cheek engaging member is a sleeve configured to receivably retain the respective connector therein.

Preferably the sleeve is configured to removably couple about the respective connector.

Preferably the connector is adapted to extend through a passage in the sleeve.

Preferably each connector is substantially housed by the respective sleeve in a region adapted to locate adjacent the user's cheek in use.

Preferably each sleeve is curved along at least a portion of the length of the sleeve to complement the contour of the respective cheek.

Preferably each connector is curved along at least a portion of the length of the connector adapted to locate adjacent the respective cheek.

Preferably the connector is preformed with a curved profile.

Preferably each sleeve is preformed with a curved profile. Alternatively each sleeve is curved upon encapsulating the respective connector.

Preferably the connector comprises a clip for releasably connecting with the patient interface.

Preferably each connector is frictionally or mechanically engaged with the respective cheek engaging member once in-situ.

Preferably each connector is configured to couple a corresponding formation on a corresponding side of the patient interface.

Preferably each connector comprises a lateral projection at an end of an elongate body, the lateral projection configured to engage the corresponding formation via a push-fit type arrangement.

Preferably the elongate body is configured to be received and retained within a channel of the corresponding formation and the projection is configured to engage an abutment surface at an exit aperture of the channel.

Preferably the channel is capable of elastic deformation for receiving the connector and for allowing the connector to be rotated axially through about 180° to enable ease of removal of the connector from the channel.

Preferably when the connector is rotated through about 180° within the channel the lateral projection of the connector becomes disengaged from the abutment of the exit aperture of the channel.

In a fourth aspect the invention may broadly be said to involve a nasal cannula comprising:
- a face mount part having a base portion and at least one elongate wing portion extending laterally from a side of the base,
- at least one nasal prong extending transversely from the base portion and capable of fitting in at least one of a user's nares, and
- wherein each wing portion comprises an exterior surface adapted to contact a portion of a user's face in use, and an elongate ridge extending transversely along the wing portion from a side of the wing portion opposing the exterior surface to aid in stabilising the face mount part upon the user's face in use.

Preferably the face mount part comprises a pair of wing portions extending laterally from either side of the base.

Preferably the face mount part comprises a pair of nasal prongs for fitting in each of the user's nares.

Preferably the elongate ridge of each wing portion extends along an upper region of the wing portion.

Preferably each wing portion comprises an accentuated terminal end extending in a direction substantially towards the user's respective cheek in use.

Preferably the terminal end of each wing portion is angled obtusely relative to a longitudinal orientation of the base portion.

Preferably the terminal end of each wing portion is of a substantially greater contact surface area than a contact surface area of the wing portion adjacent the base portion.

Preferably the terminal end of each wing portion tapers outwardly.

Preferably a distal end of each wing portion comprises a formation configured to releasably couple a complementary connector of a headgear associated with the cannula.

Preferably each connector comprises a lateral projection at an end of an elongate body, the lateral projection configured to engage the corresponding formation via a push-fit type arrangement.

Preferably the formation comprises a channel with an entry aperture and an exit aperture, and having an abutment surface at the exit aperture, and the connector comprises an elongate body is configured to be received and retained within the channel and wherein the projection is configured to engage the abutment surface at the exit aperture of the channel for retaining the connector therein.

Preferably the channel is capable of elastic deformation for receiving the connector and for allowing the connector to be rotated axially through about 180° to enable ease of removal of the connector from the channel.

Preferably when the connector is rotated through about 180° within the channel the lateral projection of the connector becomes disengaged from the abutment of the exit aperture of the channel.

Preferably the nasal cannula further comprises a bridge extending from the base portion to a lower region of the wing portion and forming a side entry on either side of the bridge.

Preferably the nasal cannula further comprises a gases flow manifold part having a gases inlet for receiving a flow of gas from a gas source, and a gases outlet for delivering the flow of gas to the at least one nasal prong of the face mount part, the manifold part being adapted to be received by the base portion through either side entry of the face mount part to fluidly connect the outlet of the manifold with the nasal prongs of the face mount part.

Preferably the face mount part further comprises a recess formed in an interior of the base portion, and the gases flow manifold part comprises a corresponding lip at the outlet adapted to releasably engage the recess to fluidly connect the outlet with the nasal prongs of the face mount part.

In a fifth aspect the invention may broadly be said to involve a nasal cannula assembly comprising:
- a face mount part having a base portion and at least one nasal prong extending from the base portion and capable of fitting in at least one of a user's nares, and
- a gases flow manifold part having a gases inlet for receiving a flow of gas from a gas source, and a gases outlet for delivering the flow of gas to the at least one nasal prong of the face mount part, the manifold part being adapted to be received by the base portion of the face mount part to fluidly connect the outlet of the manifold with the at least one nasal prong of the face mount part, and wherein the manifold part further comprises a groove at the outlet to establish a gap between the base portion of the face mount part and the manifold part in a region of the base portion configured to locate adjacent a user's philtrum in use to thereby eliminate or at least alleviate pressure on the user's septum from the manifold part in use.

Preferably the gases flow manifold part is formed from a relatively harder material than the face mount part.

Preferably the gases flow manifold part is formed from a substantially rigid plastics material, such as Polycarbonate.

Preferably the face mount part is formed from a substantially soft plastics material, such as Silicone.

Preferably the groove at the outlet of the manifold part is formed by a pair of opposed recesses on either side of a periphery of the outlet.

Preferably the periphery of the outlet of the manifold is adapted to sealably engage an interior of the base portion of the face mount part.

Preferably the outlet of the manifold part comprises a lip extending about the periphery of the outlet and the interior of the base portion comprises a corresponding recess adapted to releasably receive the lip of the outlet of the manifold part.

Preferably the face mount part comprises at least one substantially horizontal side entry passage to the interior of the base portion for releasably receiving the outlet of the manifold part therethrough.

Preferably the face mount part comprises a pair of opposed side entry passages to the interior of the base portion, each adapted to releasably receive the outlet of the manifold part therethrough.

Preferably the face mount part comprises a pair of nasal prongs.

Preferably the base portion of the face mount part comprises a dipped region between the nasal prongs to extend the base portion away from the user's septum and further alleviate pressure on the septum in use.

In a sixth aspect the invention may broadly be said to involve a patient interface comprising a nasal cannula in accordance with any combination of the fourth or fifth aspect and any combination of the one or more preferred or alternative features and/or embodiments of those aspects.

In a seventh aspect the invention may broadly be said to involve a headgear in accordance with any combination of the first, second or third aspect and any combination of the one or more preferred or alternative features and/or embodiments of those aspects.

Preferably the headgear further comprises a head band adapted to extend over the user's crown.

Preferably a strap of the headgear is formed from an elastic material.

Preferably a strap of the headgear is formed from a textile material.

In an eighth aspect the invention may broadly be said to involve a respiratory assistance system comprising:
- a patient interface in accordance with the sixth aspect for delivering a flow of humidified gas to a patient, and
- a headgear in accordance with the seventh aspect, including any combination of the preferred features there under, for retaining the patient interface upon the patient's face.

Preferably the respiratory assistance system further comprises a ventilator adapted to generate a flow of gases, and a humidifier coupled to the outlet of the ventilator for humidifying the flow of gases.

Preferably the respiratory assistance system further comprises an inspiratory conduit adapted to couple between the humidifier and the patient interface.

Preferably the respiratory assistance system further comprises an extension tube adapted to couple between the inspiratory conduit and the patient interface.

Preferably the respiratory assistance system further comprises a retention clip adapted to couple about the extension tube and to the headgear to thereby tether the tube to the headgear and relocate at least a portion of a pull force on the extension tube from by the patient interface to the headgear.

In a ninth aspect the invention may broadly be said to involve a method of disconnecting a headgear comprising at least one connector at a terminal end of the headgear from a patient interface comprising an elastically deformable formation for receiving and retaining the connector, the method comprising the steps of:
- rotating the connector axially within the formation to alter the orientation of the connector, and
- pulling the connector away from the formation to disengage the connector from the patient interface.

Preferably the step of rotating the connector comprises rotating the connector axially approximately 180 degrees.

Preferably the connector comprises an elongate body and a lateral projection extending from the body, and the corresponding formation of the patient interface comprises a channel having an entry aperture and an exit aperture and an abutment surface at a periphery of the exit aperture, and wherein the step of rotating the connector axially comprises rotating the connector to disengage the projection from the abutment surface, and the step of pulling the connector comprises pulling the connector through the channel and out of the entry aperture.

Preferably the headgear comprises a connector at either end of the headgear, and the patient interface comprises a corresponding formation at either side of the interface.

In a further aspect, there is a patient interface comprising a nasal cannula assembly and a headgear, said interface comprising:
- the nasal cannula assembly comprising:
  - a face mount part having a base portion and at least one nasal prong extending from the base portion and capable of fitting in at least one of a user's nares, and
  - a gases flow manifold part having a gases inlet for receiving a flow of gas from a gas source, and a gases outlet for delivering the flow of gas to the at least one nasal prong of the face mount part, the manifold part being adapted to be received by the base portion of the face mount part to fluidly connect the outlet of the manifold with the at least one nasal prong of the face mount part, and wherein the manifold part further comprises a groove at the outlet to establish a gap between the base portion of the face mount part and the manifold part in a region of the base portion configured to locate adjacent a user's philtrum in use to thereby eliminate or at least alleviate pressure on the user's septum from the manifold part in use, and
- the headgear for a patient interface comprising:
  - a strap forming a part of the headgear for assisting in retaining or stabilising of a patient interface upon a user,
  - wherein the strap, or a section of the strap, to be located upon or to be placed in contact with the face or a portion of a user's face includes a surface region for frictionally engaging with the user's face, the surface region being of a relatively higher frictional surface material than the remainder of the strap forming the or a part of the headgear.

According to the above aspects, the nasal cannula as defined above may include or comprise any one or more of the features as described herein.

According to the above aspects, the headgear for a patient interface as defined above may include or comprise any one or more of the features as described herein.

The term "cheek" as used in this specification and claims means any region on the user's face at or adjacent the cheekbone, and may include any region to the side of and/or below the cheekbone and/or may include any other region between by the periphery of the corresponding eye, ear and nose of the user.

The terms "upward", "across", and "rearward" as used in this specification in relation to an interface mean (unless the context indicates otherwise) approximately vertical, transversely horizontal, and front to back horizontal through or in relation to the interface when worn by a user standing upright.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF DRAWINGS

Preferred embodiments of the invention will be described by way of example only and with reference to the drawings, in which.

DETAILED DESCRIPTION

The patient interface and headgear of the present invention provide improvements in the delivery of respiratory care with a ventilator or a gases supply.

The preferred forms of patient interface and/or headgear will be described with reference to an in-hospital respiratory care system to be used by adults and/or in paediatrics. It will be appreciated that the described patient interface and/or headgear embodiments can alternatively be used in delivering CPAP therapy.

It will also be appreciated that various aspects of the present invention may be applied to any form of patient interface including, but not limited indirect nasal masks (which covers the nose), direct nasal nasal masks including nozzles or pillows enter or engage the nares of the wearer, oral masks (which cover the mouth), or full face masks (which cover the nose and mouth), and mouthpieces but will be described with reference to a nasal cannula. Similarly, various aspects of the present invention may be applied to any form of headgear but these will be described with reference to a head strap.

Figure 1:
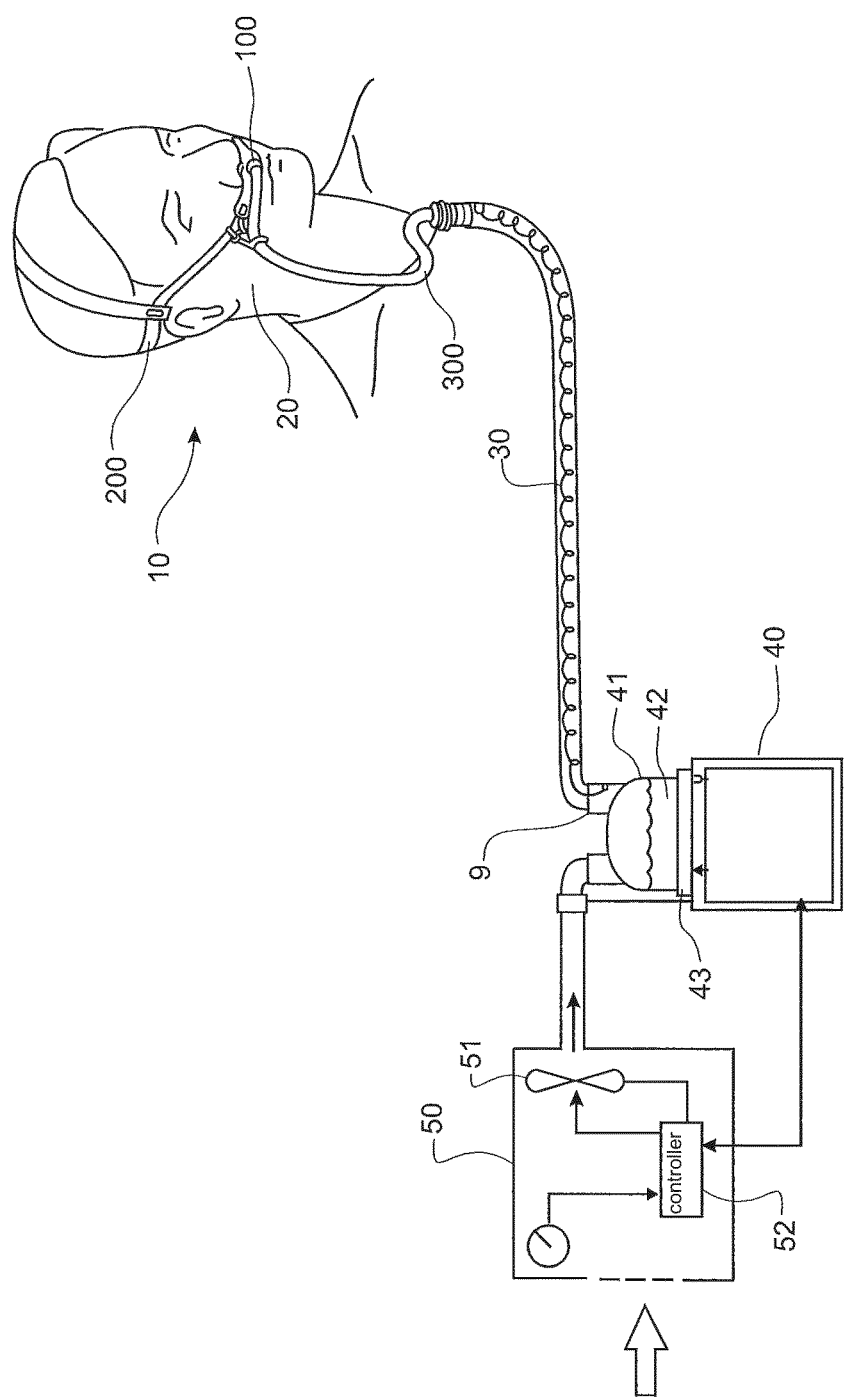
FIG. 1 is a schematic of an overall respiratory assistance system.

Referring to FIG. 1, a ventilation and humidification system (a respiratory system 10) as may be used with the present invention is shown. In such a system 10, a patient 20 is supplied with a humidified flow of gases through a patient interface 100. The patient interface 100 is retained in an operational position upon the patient's face using associated headgear 200. The interface 200 is connected to a humidified gases transportation pathway or inspiratory conduit 30. The inspiratory conduit 30 is connected at one end (either directly or indirectly) to the patient interface 100 and at an opposing end to the outlet of a humidifier 40. In the preferred embodiment the inspiratory conduit is connected to the patient interface via an extension tube/conduit 300. The humidifier 40 receives and humidifies gas supplied from a gases supply source 50, preferably including a blower 51. The humidifier 40 may comprise a humidification chamber 41 filled with water 42 and a heating means 43 for heating the water to humidify the gas path through the humidifier. A controller 52 may be provided to control and possibly vary one or more properties of the supplied gas, including but not limited to the pressure profile of the gas, the flow rate profiles of the gas at the patient interface, the temperature of the gas and/or the humidity of the gas. It will be appreciated that the control capabilities are dependent on the purpose and application of the respiratory system 10. For example, in the preferred application of in-hospital respiratory care, the flow rate of supplied gas is monitored and controlled according to the patient's requirements but the pressure of the supplied gas is not necessarily monitored and controlled. In alternative embodiments, such as the use of the invention in a CPAP, the pressure profile of the supplied gas may be monitored and controlled.

Preferred embodiments of the invention will now be described for the patient interface 100 and the headgear 200. Other aspects of the respiratory system 10 will not be described in detail to maintain conciseness, however, it will be appreciated that these aspects can take on any desired form known in the art to effect appropriate operation of the overall respiratory system 10 without departing from the scope of this invention.

Referring to FIGS. 2-11, preferred forms of the headgear 200 and of the patient interface 100 are shown. The embodiments show a patient interface 100 configured to deliver breathing gases from a gases supply and humidification source (not shown) to the patient, and headgear 200 configured to support and retain the patient interface against the patient's face in use. The patient interface 100 of the preferred embodiment is in the form of a nasal cannula 100 that is adapted to couple an inspiratory conduit 300 and that comprises at least one, but preferably two, nasal prongs 111 and 112 configured to fit within the nares of a patient to deliver a flow of gases to the patient. The headgear 200 is in the form of a head strap 200 that is preferably adjustable in length to customise the size of the strap to the patient.

The gas supply tube shown as item 300 is preferably a breathable tube. For example, is advantageously a robust and generally long-lasting tube.

Nasal Cannula

Referring to FIGS. 2-4, the nasal cannula 100 provides a patient with a patient interface suitable for the delivery of high airflow, high humidity gas flow to the patient's nasal cavity/nares. In some configurations, the cannula is adapted to deliver a high flow of gases over a wide flow range (e.g. may preferably be about 8 L/min, or may be higher depending on other preferred therapy applications, perhaps such as 10-50 L/min). In some configurations, the cannula is adapted to deliver relatively low pressure gases.

The nasal cannula 100 comprises a face mount part 110 including at least one, but preferably a pair of tubular nasal prongs 111 and 112, integrally moulded with or removably attached to the face mount part 110, and a gases flow manifold part 120 that is removably attached or integrally moulded to the conduit 300. As will be described in further detail below, the gases flow manifold part 120 is insertable into the face mount part from either one of two opposing horizontal directions, i.e. from either left side or the right side. In this manner, the position or location of the gases flow manifold part 120 is reversible with respect to the face mount part 110. In other words, a user may choose to have the manifold part 120 (and essentially the conduit 300 extending there-from) extend from either the left side or the right side of the cannula 100 depending on what is most convenient, for example depending on which side of the user the gas source or ventilator is located.

The face mount part 100 is formed from a soft, flexible and material such as Silicone or other cannula material known in the art. The nasal prongs 111 and 112 are preferably supple and may be formed from a sufficiently thin layer of Silicone to achieve this property.

The gases flow manifold part 120 is formed from a relatively harder material such as Polycarbonate, a High-Density Polyethylene (HDPE) or any other suitable plastics material known in the art. The face mount part 110 provides a soft interfacing component to the patient for comfortably delivering the flow of gases through the nasal prongs 111 and 112, while the gases flow manifold part 120 fluidly couples the conduit 300 to the nasal prongs 111 and 112 of the face mount part 110.

Referring to FIGS. 5-8, the nasal prongs 111 and 112 are curved to extend into the patient's nares in use and to provide a smooth flow path for gases to flow through. The inner surfaces of the prongs 111 and 112 may be contoured to reduce noise. The bases of the prongs 111 and 112 may include curves surfaces to provide for smoother gases flow. This may reduce the noise level during operation.

In some configurations, pads may be mounted around the base of the prongs to reduce noise. The pad may be a foam material or a mouldable material that generally conforms to the patient's nose anatomy. Soft cushions or pillows may alternatively be provided.

The nasal prongs 111 and 112 are substantially hollow and substantially tubular in shape.

The nasal prongs 111 and 112 may be consistent in diameter along their lengths but are preferably shaped to fit the contours of the nares. Each prong 111/112 has an elongate opening 111a/112a at the distal end opposing a base portion 118 of the face mount part 110 to encourage a high flow of gases into the cavity. In alternative embodiments the nasal prongs 111 and 112 may have a tapered profile of a wider end at the base portion 118 and a narrower end at the openings 111a and 112a.

The openings 111a and 112a may be scooped to direct the flow of gases up the patient's nares. The face mount portion 110 and in particular the nasal prongs 111 and 112 are preferably designed not to seal about the patient's nares to avoid excessive and potentially harmful build up of pressure during high flow therapy. The nasal prongs 111 and 112 are therefore sized to maintain a sufficient gap between the outer surface of the prongs 111 and 112 and the patient's skin to avoid sealing the gas path between the cannula 100 and patient.

The face mount part 110 is shaped to generally follow the contours of a patient's face around the upper lip area. The face mount part 100 is moulded or pre-formed to be able to conform to and/or is pliable to adapt, accommodate and/or correspond with the contours of the user's face, in the region of the face where the cannula is to be located.

The face mount part 110 comprises an elongate base portion 118 from which the nasal prongs 111 and 112 extend, and two wing portions 113 and 114 extending laterally from either side of the base portion 118. The wing portions 113 and 114 are integrally formed with the base portion 118 but may alternatively be separate parts. An inner side 119 of the base portion 118 of the face mount part 110 is formed with an elongated oval recess 119a configured to couple a corresponding outlet of the manifold 120. An arcuate bridge 118a extends from the centre of the base portion 118 to an inner wall 113a/114a of the wings to create two horizontal side entry passages 121a and 121b for insertion of the outlet 123 of the manifold 120 from either side 121a or 121b there-through.

The gases flow manifold part 120 is generally tubular in shape having a substantially annular inlet 122 at one end, and that curves around into an elongate oval outlet 123 at the opposing end. The inlet 122 is preferably removably attachable to the conduit 300, preferably via a threaded engagement but alternatively via a snap-fit or any other type of coupling known in the art. Alternatively, the inlet is fixedly coupled or integrally formed with the conduit 300. The shape of the outlet 123 corresponds with and fits into the elongate recess 119a of the face mount part 110 with a friction fit or snap fit engagement, such that substantial force, or at least a deliberate force applied by a user or a carer, is required to separate the manifold 120 from the face mount part 110.

Desirably, the inadvertent disengagement of the manifold from the face mount part is to be avoided.

An effective seal is also formed between the outlet 123 and the base portion 118 upon engagement of the two parts 110 and 120. In particular, an outer rim or lip 126 is formed about the outlet 123 which corresponds with and sealably fits into an inner groove about the periphery of the inner recess 119a to retain the outlet of the manifold 120 within the face mount part 110. Upon coupling the parts 110 and 120, the upper surface of the lip 126 engages an inner surface 119b of the base portion 118/surface 119b of the recess 119a to form an effective seal between the parts 110 and 120 for gases to flow there through. The nasal prongs 111 and 112 are aligned with corresponding apertures extending through the surface 119b of the base portion 118 to the recess 119a to fluidly connect the manifold outlet 123 with the nasal prongs 111 and 112 when coupled. The bridge 118a whilst defining the entry passages 121a and 121b for the manifold 120, also helps to retain the manifold 120 within the base 118 of the face mount part 110. A corresponding indent 128 is formed on the outer surface of the outlet 123 with opposed ridges 129a and 129b on either side to provide a push-fit engagement mechanism between the outlet 123 and the bridge 118a of the face mount part 110.

The exterior surface of the face mount portion and/or the wings 111 and 112 may comprises one or more channels to facilitate or allow air to flow between the lip and the cannula to cool the patient.

Adhesive pads may be provided on each wing 111 and 112 to facilitate coupling of the cannula 100 to the patient—especially for younger children (e.g. under 5 years old).

Ridges on Wings

Each wing portion 113/114 extends laterally from the base portion 118 of the face mount part 110 and comprises an outer surface 113b/114b configured to contact against the patient's face in use, preferably at least the upper lip region of the patient's face and slightly beyond towards the user's respective cheek. The distal ends 113c and 114c of the wings 113 and 114 are configured to releasably connect respective end portions 201 and 202 of the head strap 200 to retain the face mount portion 110 against the patient's face.

In the preferred embodiment, each wing 113/114 comprises an integral ridge 115/116 extending transversely along the length of the wing 113/114 from the inner side of the face mount part 110 opposing the outer surface 113b/114b of the wing 113/114. In the preferred embodiment, each ridge 115/116 is substantially perpendicular to the outer contact surface 113b/114b of the respective wing 113/114. Each ridge 115/116 preferably extends from the base portion 118 of the face mount part 110 and along an upper region of the respective wing 113/114. The ridge 115/116 acts to stabilise the face mount part 110 against the patient's face and minimise torsional stress which could otherwise cause the nasal prongs 101 and 102 to turn out and away from patient's nares. The dimensions of the ridge 115/116 including any combination of length, thickness and width (i.e. the extent to which the ridge extends away from the outer surface 113b/114b), should be sufficient to improve the stabilisation of the face mount part 110 upon the patient's face.

The ridge 115/116 may be over-moulded or integrally formed with the respective wings 113/114 of the face mount part 110.

Accentuated Wings

In the preferred embodiment, the distal or terminal end 113c/114c of each wing 113/114 is accentuated or formed with a substantially greater contact surface area than a contact surface area of the wing 113/114 in the region adjacent the nasal prongs. This distal end portion 113c/114c is preferably also angled relative to a general longitudinal axis of the face mount part 110 or base 118. In particular, the distal end portion 113c/114c extends obtusely away from the base 118, or from a region of the respective wing 113/114 adjacent the base, and towards the patient's respective cheek in use. In this manner, connecting the head strap 200 to the distal end portions 113c and 114c of the wings 113 and 144 and wearing the interface 100 will create a substantially V-shaped structure that generates a force vector acting on the wings 113 and 114 and cannula 110 in the direction of the patient's cheeks. This has the effect of improving retention of the nasal prongs 111 and 112 within the patient's nares and will cause the prongs 111 and 112 to turn into the nares when the distal ends 113c and 114c of the wings 113 and 114 are pulled by the respective ends 201 and 202 of the headgear 200. Each distal end portion 113c/114c may be angled smoothly or rounded or it may be angled sharply or abruptly relative to the remainder of the respective wing 113/114.

In the preferred embodiment, the distal end portion 113c/114c is outwardly tapered to enlarge the contact surface area of the respective wing 113/114 and to also angle the distal end 113c/114c towards the patient's cheeks.

The increased surface area at the distal ends 113c and 114c provides added real estate for forming a suitable connection mechanism to couple the head strap 200. In the preferred embodiment, clip retention formations 101 and 102 are provided at each distal end 113c/114c to releasably couple clip components of the head strap 200 to the face mount portion 110 of the cannula 100.

Recessed Manifold

A patient's septum and/or columalla is generally quite a sensitive area and can be a source of discomfort when subjected to excessive contact pressure for prolonged periods. The present invention alleviates or reduces this pressure by providing a cushioned region of the cannula 100 adjacent the patient's septum/columalla. In the preferred embodiment, the outlet 123 comprises a pair of opposed recesses or grooves 124/125 at the outer periphery for forming a dent or dip 127 in a region that locates adjacent the septum/columalla in use. When coupled to the face mount portion 110, this dip 127 creates a gap between the base portion 118 and the outlet 123 of the manifold 120. In use, the gap cushions/softens the region of the cannula 100 directly adjacent the septum/columalla. It disengages the pressure of the harder manifold part 120 from the septum/columalla and allows the septum/columalla to rest on the soft base of the face mount portion 110 only.

The base portion 118 is preferably also formed with a hollowed outer portion and/or dipped outer profile 118b between the prongs 111 and 112 to alleviate pressure at the septum/columalla. The hollowing should be as much as possible without (significantly) compromising the flow delivered to the patient. The dipped portion 118b is also preferably complementary to the periphery of the outlet 123 to maintain an effective seal between the two parts of the cannula.

Head Strap

Referring now back to FIGS. 2-4, in the preferred embodiments the headgear used to retain the patient interface 100 against the patient's face comprises a head strap 200 of a single continuous length and adapted to extend in use along the patient's cheeks, above the ears and about the back of the head.

Primary end portions 201 and 202 of the strap 200 are adapted to releasably connect respective formations 101 and 102 on either side of the nasal cannula 100 to hold the cannula 100 in position during use.

In a preferred embodiment, a clip component is provided at each end portion 201/202 capable of being received and retained within the corresponding formation 101/102. The clip component may be coupled to the strap at the respective primary end portion in accordance with one of two preferred embodiments (as will be described in further detail below). Furthermore, the head strap 200 is adjustable in length to help customise the strap to the wearer's head. Three different head strap adjustment configurations are described below in accordance with three preferred embodiments of the invention. In each of the embodiments, the strap 200 is preferably formed from a soft and stretchable/elastic material such as an elastic, textile material/fabric that is comfortable to the wearer. Alternatively, the strap 200 may be formed from a substantially more rigid, or less flexible, material such as a hard plastics material.

In any one of the embodiments described below, the headgear 200 may further comprise an additional strap or other headgear component that couples the strap 200 to extend over the patient's crown in use (as shown in FIG. 1). A crown strap or crown component can have the benefit of pulling the strap 200 up and above the patient's ears in use to improve fit and comfort.

First Embodiment

Figure 2A:
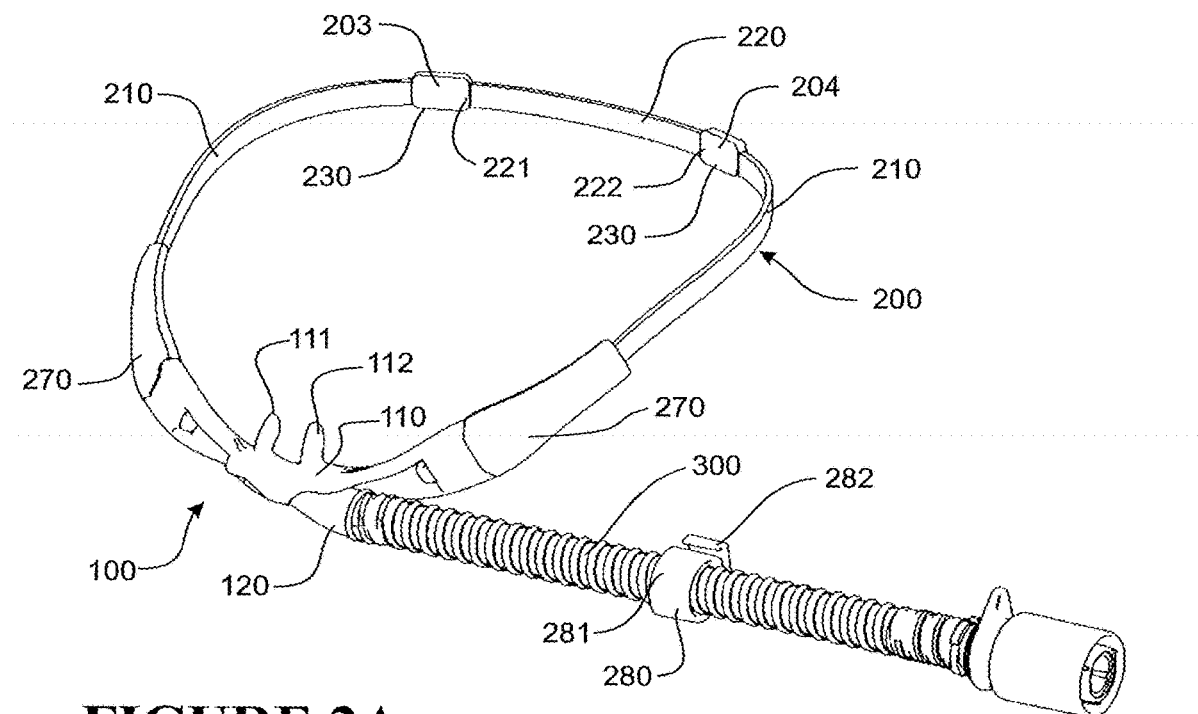
FIG. 2A is a perspective view of a preferred form patient interface and a first preferred form headgear of the invention in the assembled state.
Figure 2C:
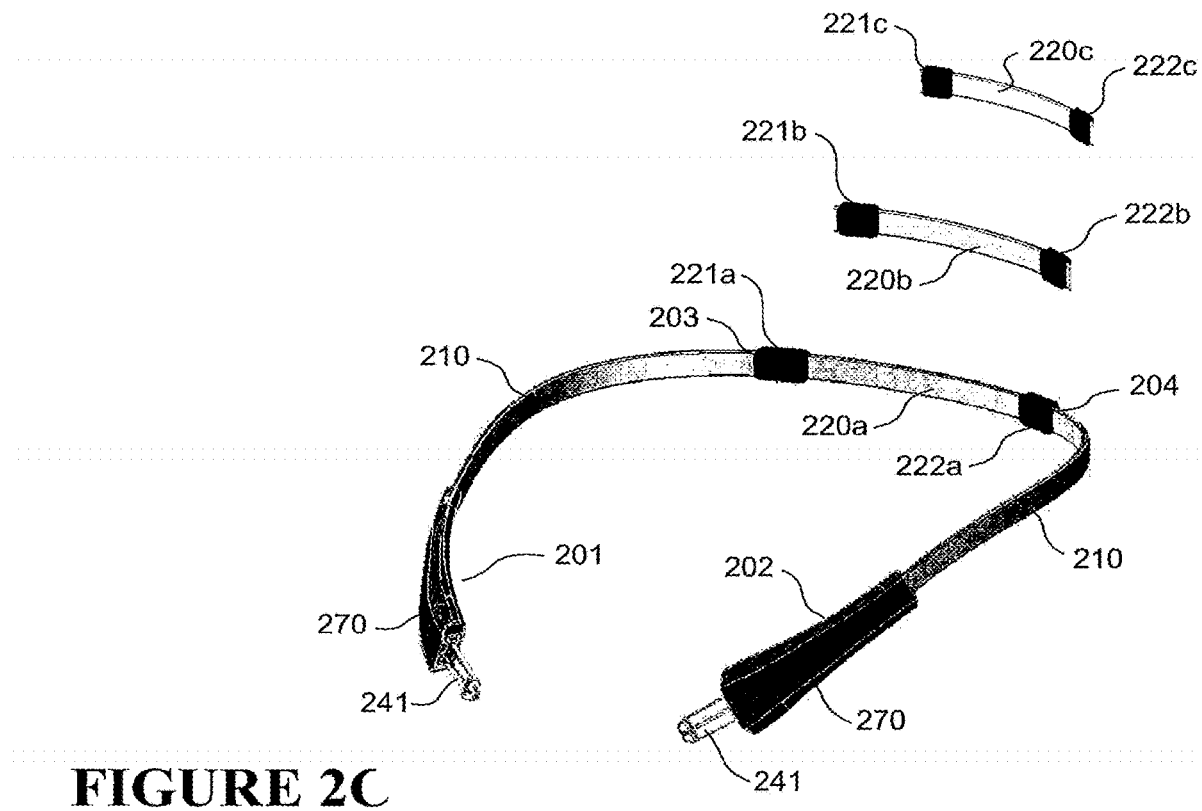
FIG. 2C is a perspective view of the headgear of FIG. 2A with a range of strap extension options.
Figure 2B:
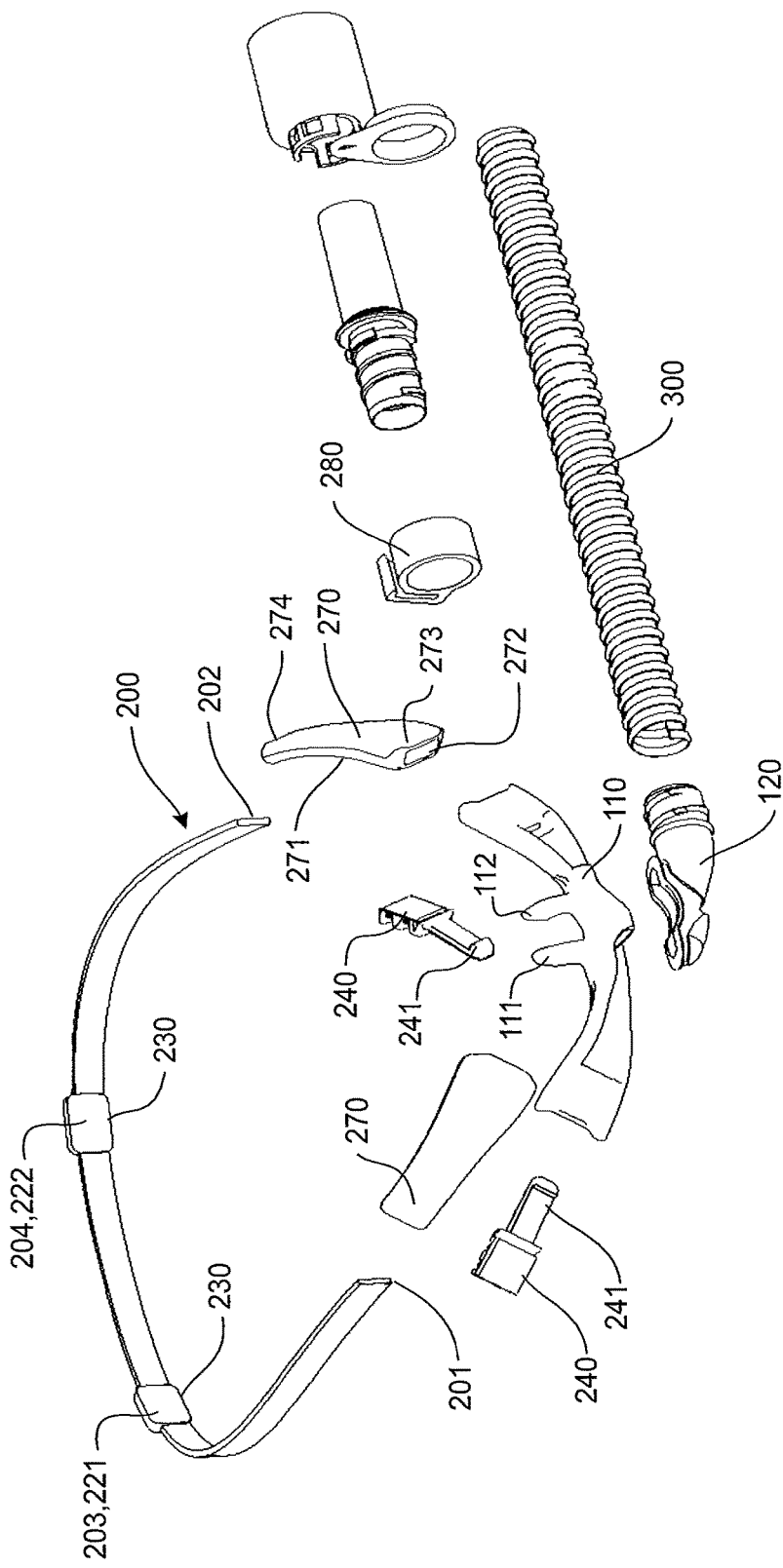
FIG. 2B is a perspective view of the patient interface and headgear of FIG. 2A in the disassembled state.

Generally, but also with reference to FIGS. 2A-2C, in the first preferred embodiment of an adjustable strap 200 the adjustment mechanism is provided in the form of one or more insertable/removable strap segments or strap extensions 220.

Strap segments 220 of a fixed length can be releasably connected to the main strap 210 to extend its length. The main strap 210 in this embodiment comprises a pair of intermediate or secondary end portions 203/204 that are releasably connectable with one another, and that are also releasably connectable with respective ends 221 and 222 of the strap segments 220. When the secondary end portions 203 and 204 are connected to one another, the main strap 210 is of a continuous starting length/size for the wearer. To extend the length of the strap 200 beyond this starting length, the main strap 210 can be disconnected at the secondary end portions 203/204 and one or more additional strap segments 220 are connected there between.

A number of strap segments 220 of varying predetermined lengths, 220A-220C for example, may be provided to provide alternative adjustment lengths. For example, one or more strap segments 220 may be provided having a length within the range of about 1 cm to about 10 cm, or within the range of about 2 cm to about 6 cm. The strap segments 220 have lengths of, for example, about 2 cm, about 4 cm or about 6 cm. It will be appreciated that these examples are not intended to be limiting and the length of each strap segments can be of any size as it is dependent on the user and/or application.

Furthermore, each end 221/222 of each strap segment 220 is preferably connectable to a respective end 221/222 of another strap segment 220 and/or to a respective secondary end portion 203/204 of the main strap 210 to thereby enable a user to combine one or more strap segments 220 of the same or varying lengths to customise the overall length of the extension as required/desired.

The additional strap segments are preferably formed from a soft and stretchable/elastic material such as an elastic, textile material/fabric that are comfortable to the wearer. For example, a tubular knitted type head strap or sections of the head straps 210 may be utilised, particular for comfort over a user's ears.

It will be appreciated, particular comfort may be achieved from a head strap which is able to provide suitable locating of the patient interface in a preferred relatively stable position on a user's face, yet simultaneously provide for a relatively loose fit or low tension fit about the user's head.

Alternatively, the additional strap segments may be formed from a substantially rigid material such as a hard plastics material.

A strap connector 230 is provided at each of the secondary end portions 203/204 of the main strap 210 and the respective end portions 203/204 of the strap segments 220.

Each connector 230 is provided with a strap connection mechanism at one end to couple to the strap material, and a coupling mechanism at an opposing end to releasably couple the respective end of a similar connector 230.

In an alternative, the connector 230 may be various different forms of adjustable buckles suitable for adjusting the length or tension of the head strap sections 210 which hold the patient interface in position about a user's head.

It will also be appreciated that the connector 230 may be located so as to be off-set from a mid-point from the rear of a user's head, or may be offset to one side of a user's head.

This may be advantageous so as to avoid impinging upon a part of a user's head which may otherwise be, in some positions such as sleeping, uncomfortable for the user.

In yet a further embodiment, the strap segments may be of different lengths, so as to be asymmetrically provided or to help be operational with an off-set connector 230 position. Further, it may be that of the two strap segments 210, one of those straps may be adjustable in length while the other is not. For example, one strap segment 210 may be of a permanent length or permanently connected to the connector 230.

In a preferred embodiment, the strap connection mechanism may comprise of a series of internal teeth located within the body of the connector for establishing a friction fit engagement with the respective end of the strap. A hinged jaw of the body is provided and closes upon the teeth to securely retain the end of the strap upon the teeth. The releasable coupling mechanism at the other end comprises a pair of male and female members, such as a protrusion and aperture respectively, both adapted to connect to corresponding male and female members of a similar connector 230. A lug on the protrusion may couple a recess in the female member to provide a snap-fit engagement between the members. It will be appreciated that in alternative embodiments, any other suitable connector configuration may be used to releasably connect the secondary end portions of the strap to one another, and to the end portions of the additional strap segments.

Figure 9:
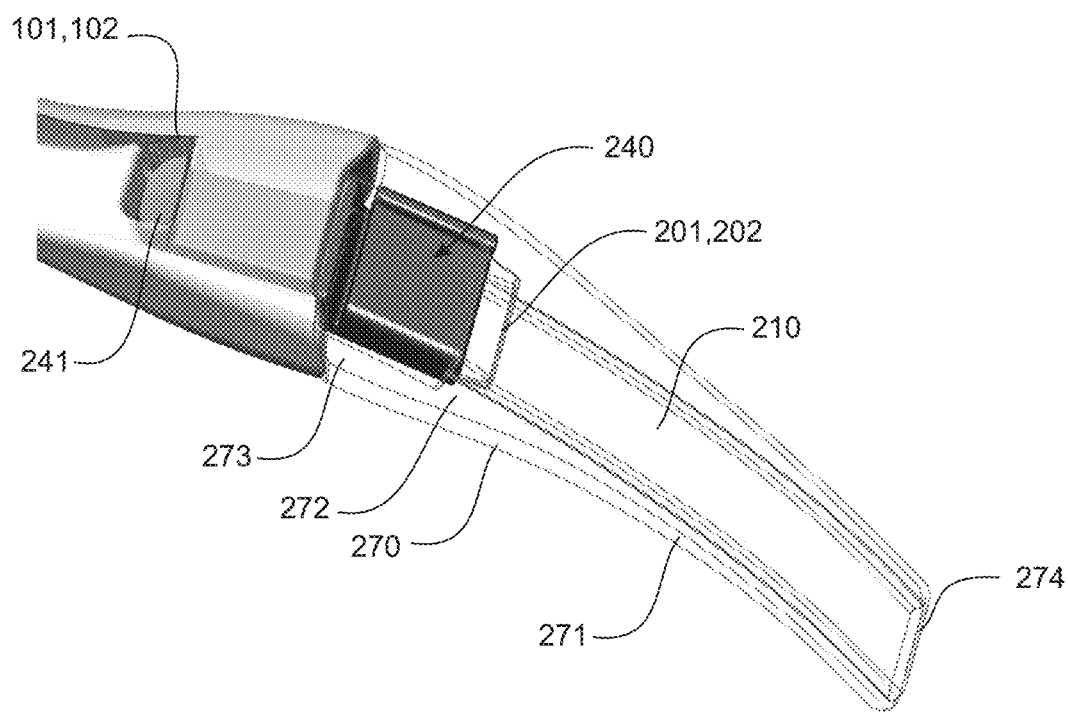
FIG. 9 is a close-up perspective view of the connection between the patient interface and the headgear of the FIGS. 3 and 4 embodiments and showing a preferred form sleeve associated the headgear.

Referring also to FIG. 9, cannula connectors 240 are provided at the primary end portions 201 and 202 of the main strap 210. These connectors 240 have a similar strap connection mechanism to the strap connectors 230 of the secondary end portions 203 and 204, but include a clip member, such as a push fit clip 241, at an end of the connector 240 opposing the strap ends. The clip 241 is configured to releasably couple the respective formation 101/102 at the side of the cannula 110. The clip member 241 is preferably a bendable part, such as a plastic part, that forms a hinged portion relative to the strap. The clip 241 is preferably preformed to have a curved shape along its length, such as one with an angle between flat and 20 degrees for example. This curve allows the clip 241 to fit the contour of the patient's face in the region of the clip 241.

Referring to FIGS. 12A-C and 13A-B, a method of engaging and disengaging each connector 240 of the head strap 200 to and from the patient interface 110 will now be described. Each connector 240 comprises a clip member 241 having an elongate connector body 242 and a lateral projection 243 at a terminal end of the body 242. The lateral projection 243 comprises an inwardly facing engagement surface 243a. The face 244 of the connector 240 opposing the face 245 from which the projection 243 extends is preferably substantially smooth or planar. The corresponding formation 101/102 of the cannula 110 comprises a channel 101a/102a having entry 101b/102b and exit 101c/102c apertures at either end of the channel 101a/102a. A peripheral wall of the exit aperture 101c/102c defines an abutment 101ci/102ci configured to engage with the surface 243a of the projection 243 of the clip member 241. A periphery 101bi/102bi of the entry aperture 101b/102b defines an abutment for engaging a flange 246 at an opposing end of the body 242 to the projection 243. This acts to limit the extent of insertion of the connector 240 into the corresponding channel 101a/102a. The flange 246 may be provided by a terminal end of the strap connection mechanism and/or the sleeve 270.

Figure 12A:
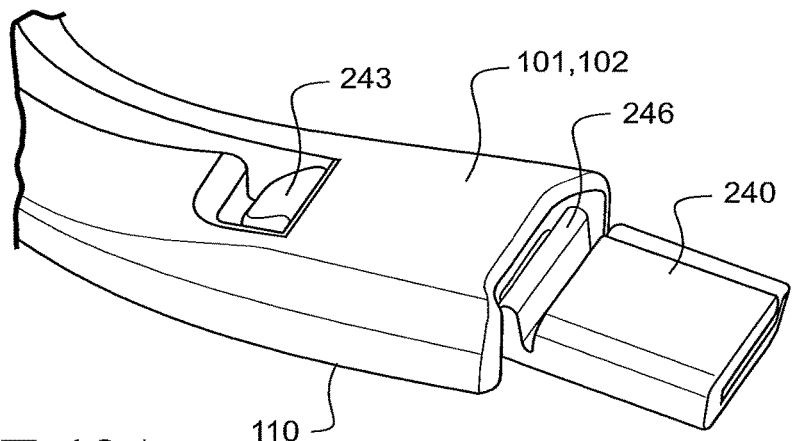
FIGS. 12A-12C show a preferred form method for removal of a connector of the first and second preferred form headgears from a patient interface.
Figure 13A:
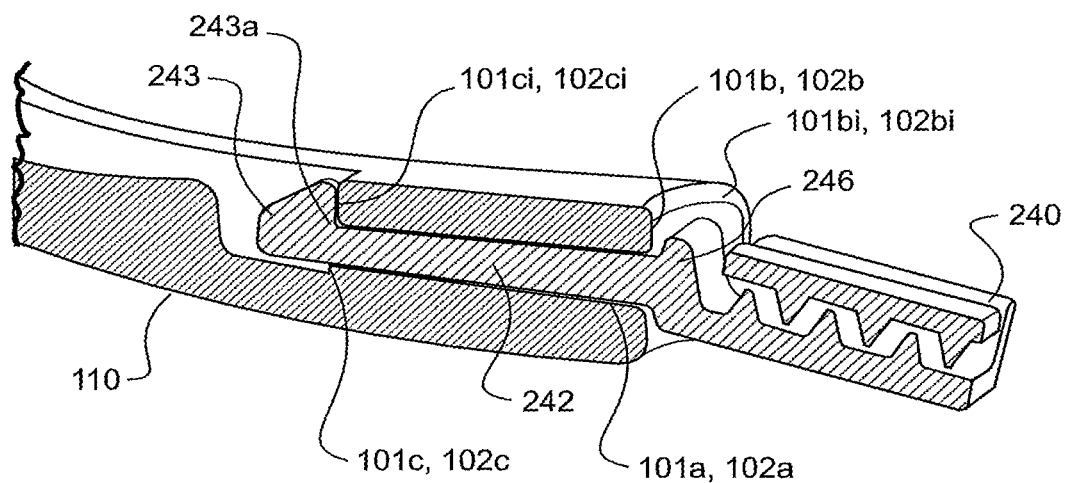
FIGS. 13A-13B show cross-sectional views of FIGS. 12A-12B respectively.

As shown in FIGS. 12A and 13A, to couple the connector 240 with the cannula 110, a user would insert the elongate body 242 through the entry aperture 101b/102b of the respective channel 101a/102a with the projection end 243 leading, until the projection 243 is caused to protrude through the exit aperture 101c/102c and engage the corresponding abutment 101ci/102ci and when the flange 246 engages the surface 101bi/102bi. To achieve engagement of the lateral projection 243 with the corresponding abutment 101ci/102ci, the user must orient the connector 240 to align with the projection 243 with the abutment 101ci/102ci.

In the preferred embodiment the abutment 101ci/102ci is at the upper peripheral wall of the exit aperture 101c/102c but in alternative embodiment the abutment 101ci/102ci may be located at any other portion of the peripheral wall of the aperture 101c/102c. For the preferred embodiment, to engage the surface 243a of the projection 243 with the abutment 101ci/102ci, a user may align the projection 243 with the upper peripheral wall of the exit aperture 101c/102c. This may be done before or after insertion of the elongate body 242 through the channel 101a/102a. In other words, the user may insert the connector 240 with the projection 243 facing in the direction of the abutment 102ci/102ci to immediately engage the surface 243a with the abutment 102ci/102ci when the projection 243 exits the channel 101a/102a through aperture 101c/102c. Or alternatively the user may insert the connector 240 with the projection 243 misaligned with the direction of the abutment 101ci/102ci, for example facing away from the abutment 101ci/102ci or 180 degrees from the direction of the abutment 101ci/102ci, and then rotate the connector 240 axially after the projection 243 exits the channel 101a/102a through aperture 101c/102c to align and engage the surface 243a with the abutment 101ci/102ci.

The engagement between the projection 243 and the abutment 101ci/102ci resists pulling forces on the connector 240 that may cause inadvertent disconnection of the connector from the cannula 110. As such the connector 240 and corresponding formation 101/102 are both configured to provide a certain level of resistance against forces acting to pull the connector 240 back through the channel 101a/102a. This resistance can prevent inadvertent removal and also make the deliberate disconnection of the connector 240 substantially difficult or cumbersome.

Figure 12B:
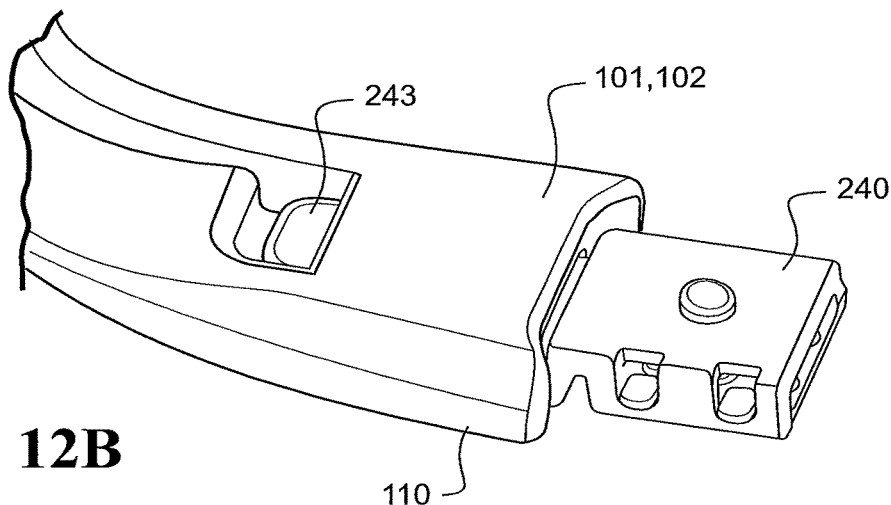
Figure 12C:
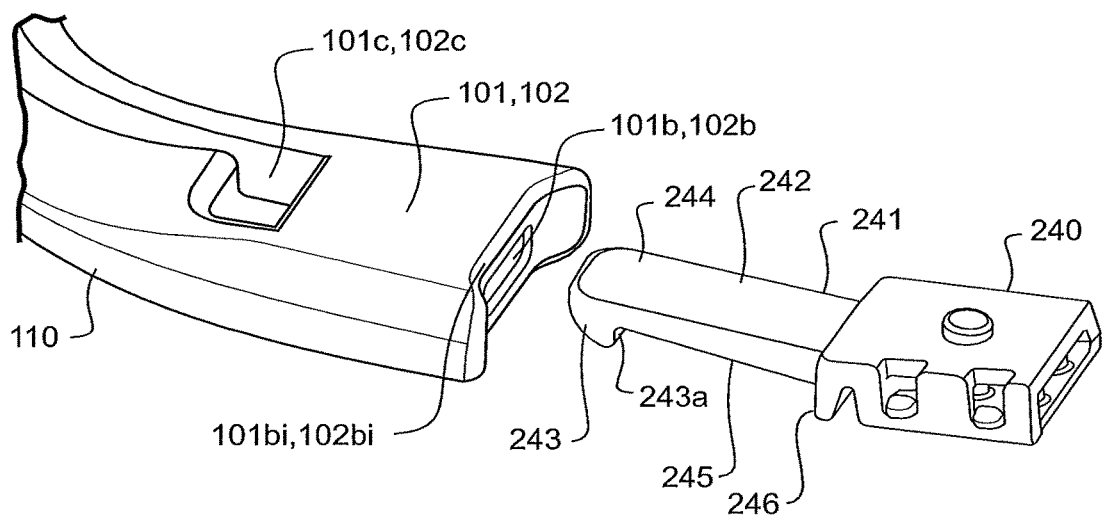
Figure 13B:
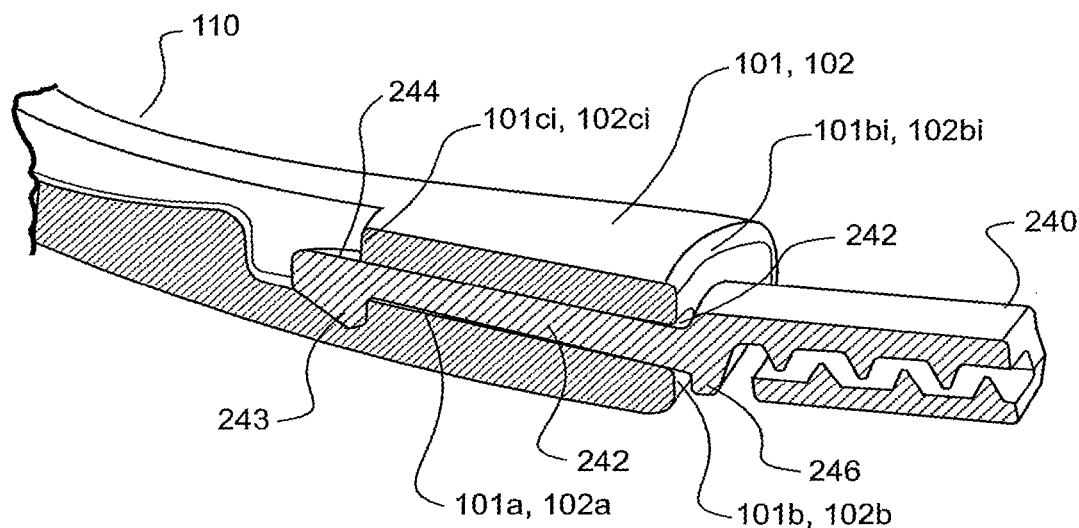
Figure 14A:
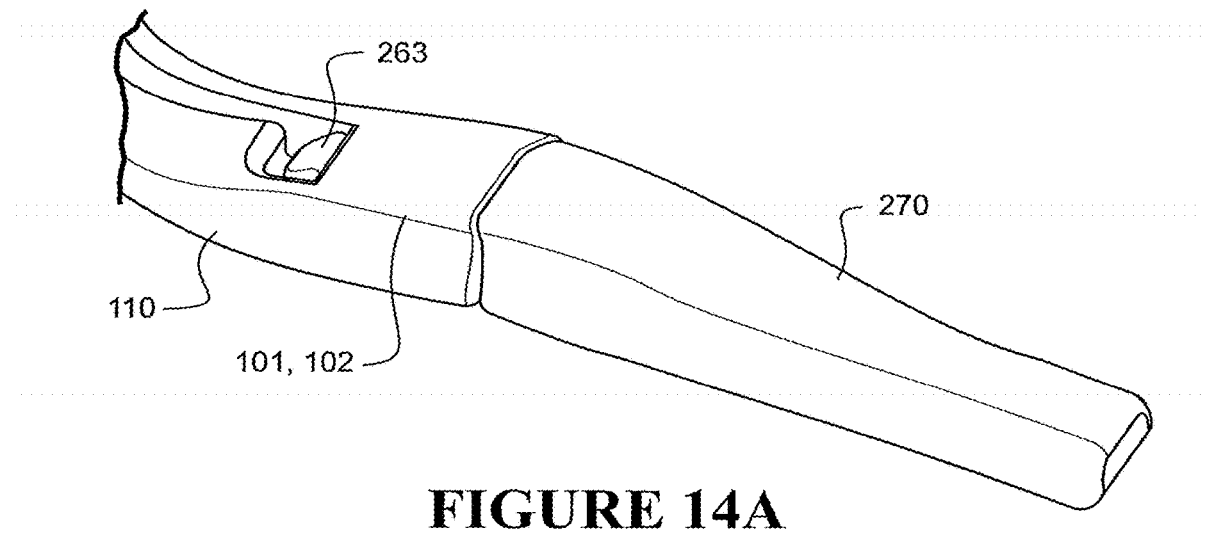
FIGS. 14A-14C show a preferred form method for removal of a connector of the third preferred form headgear from a patient interface.
Figure 14B:
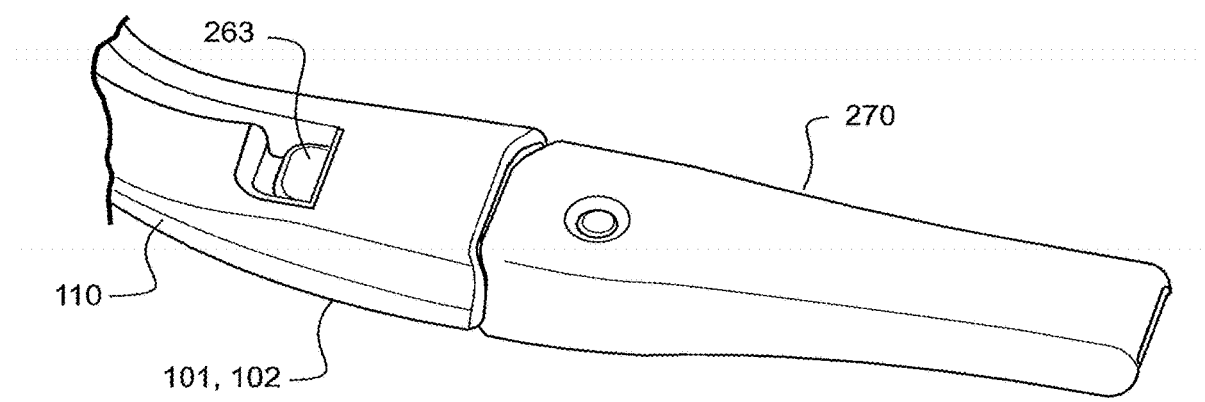
Figure 14C:
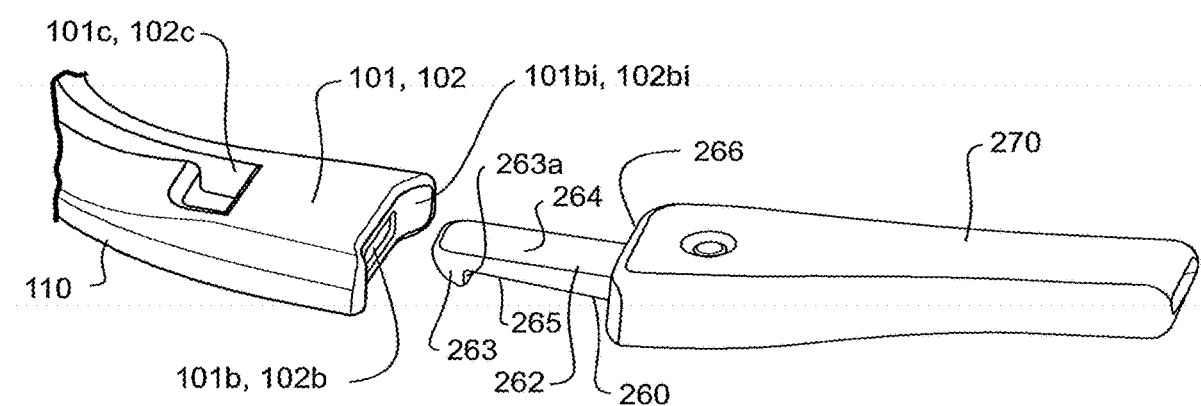
Figure 15A:
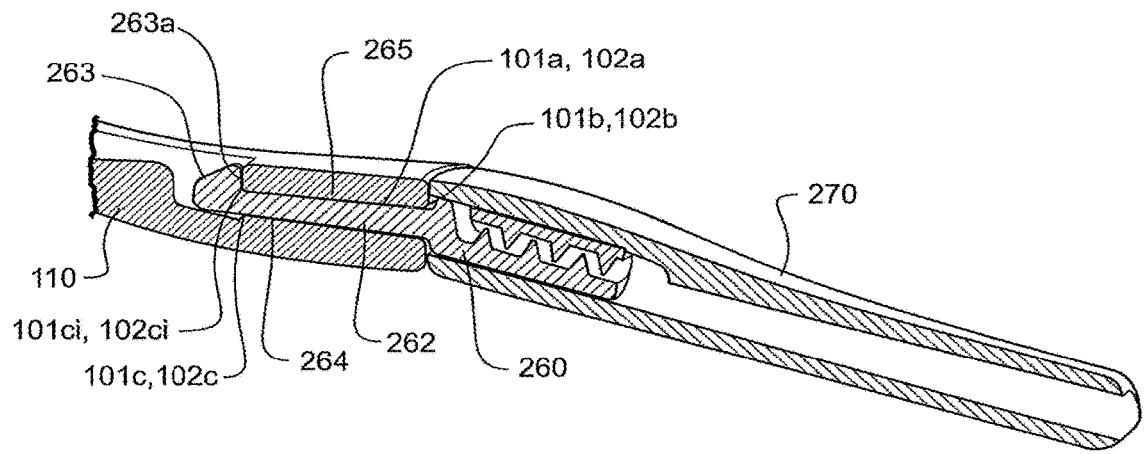
FIG. 15A-15B show cross-sectional view of FIGS. 14A-14B respectively.
Figure 15B:
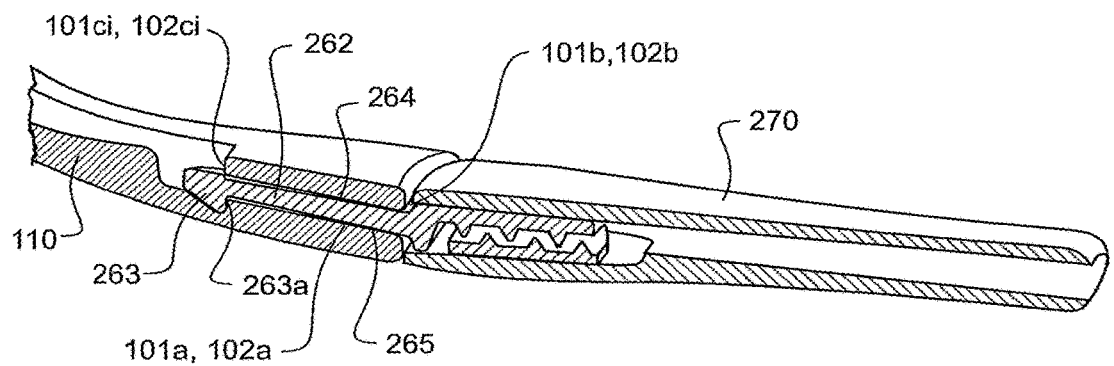

Referring now to FIGS. 12B, 12C and 13B, to avoid the additional pulling effort required, the preferred form method for removing the connector 240 from the cannula 110 comprises: rotating the connector 240 within the channel 101a/102a about its longitudinal axis to disengage the projection 243 from the abutment 101ci/102ci (FIGS. 12B and 13B), and then pulling the connector 240 out of the channel 101a/102a through the entry aperture 101b/102b (FIG. 12C). In the preferred embodiment, the projection 243 is rotated axially approximately 180 degrees away from the abutment 101ci/102ci to align the projection with a floor or opening of the channel 101a/102a, and to align the planar face 244 with the abutment 101ci/102ci and with an upper guiding wall of the channel 101a/102a. In alternative embodiments, the connector 240 may be rotated axially by another angle that sufficiently disengage the projection 243 from the abutment 101ci/102ci to reduce the resistance force against removal of the connector 240 out of the channel 101a/102a.

In the preferred embodiment, the formations 101 and 102 are elastically flexible, and preferably integral with the elastically flexible cannula 110, relative to the substantially more rigid connectors 240. As such during insertion or removal, when the connector 240 is rotated axially about its longitudinal axis, the channel 101a/102a of the formation 101/102 is caused to elastically deform to enable rotation.

Second Embodiment

Figure 3A:
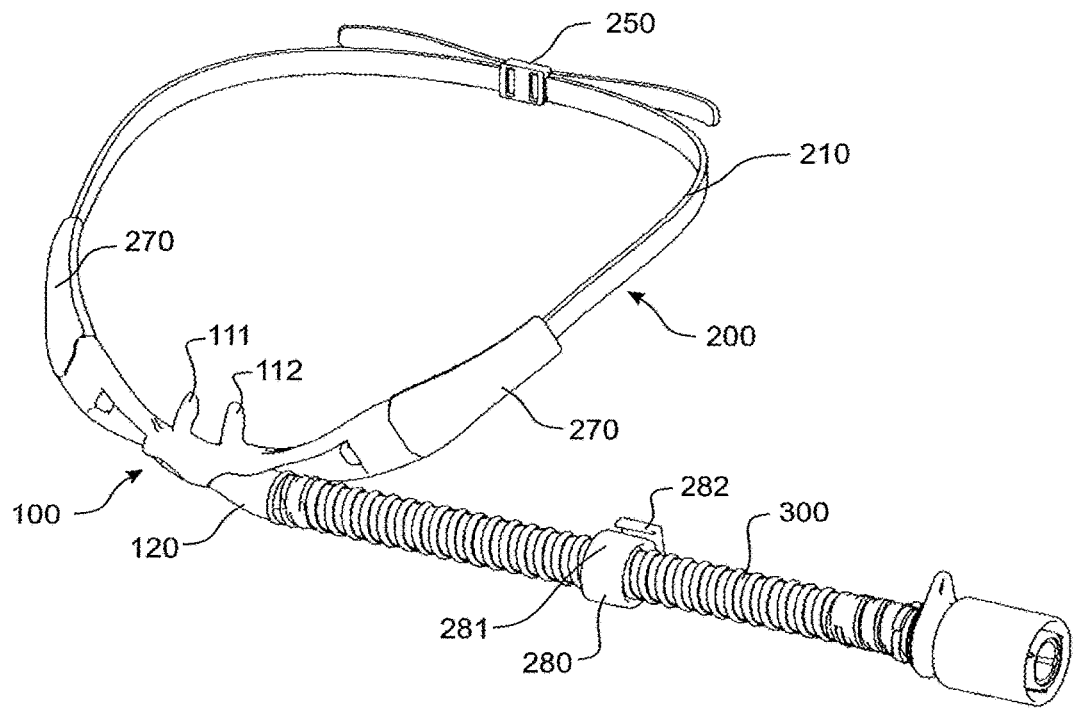
FIG. 3A is a perspective view of a preferred form patient interface and a second preferred form headgear of the invention in the assembled state.
Figure 3B:
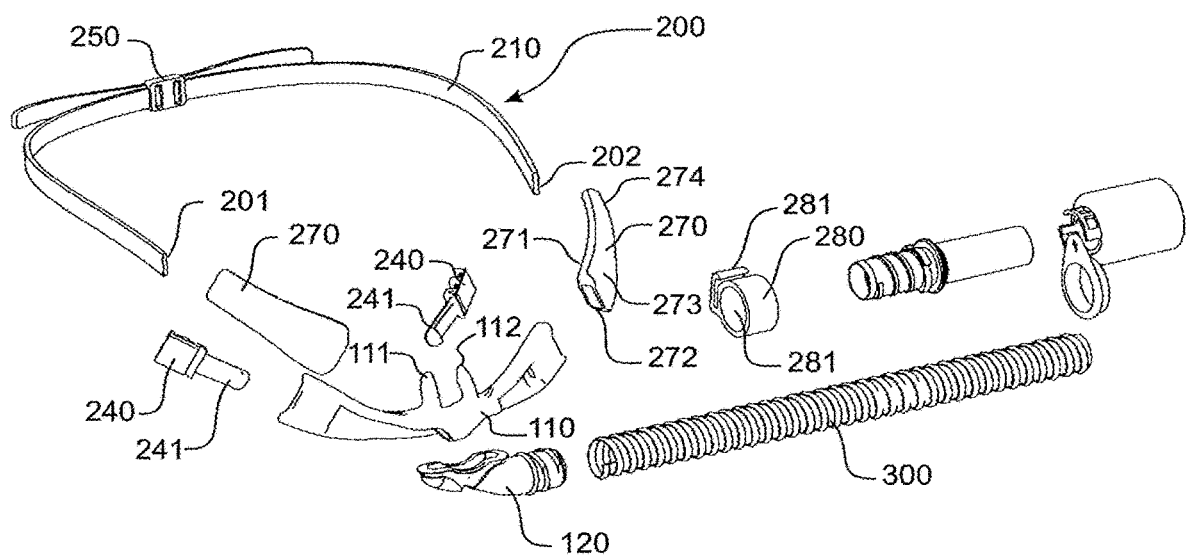
FIG. 3B is a perspective view of the patient interface and headgear of FIG. 3A in the disassembled state.

In the second preferred form shown in FIGS. 3A and 3B, a single strap is provided with the adjustment mechanism comprising an adjustment buckle 250. The strap is looped about the adjustment buckle 250 as is well known in the art and manipulated by the wearer by pulling on the appropriate portion of the strap 210 to adjust the effective length. The adjustment buckle 250 is located in a central region of the strap 200 that locates adjacent the rear of the patient's head in use.

In this embodiment the cannula connectors 240 at the primary end portions 201 and 202 are of the same configuration as cannula connectors 240 described for the first embodiment. The same method of insertion and/or removal of the connectors 240 into and/or from the cannula 110 as the one described above for the first headgear embodiment is applicable to this embodiment.

Third Embodiment

Figure 4A:
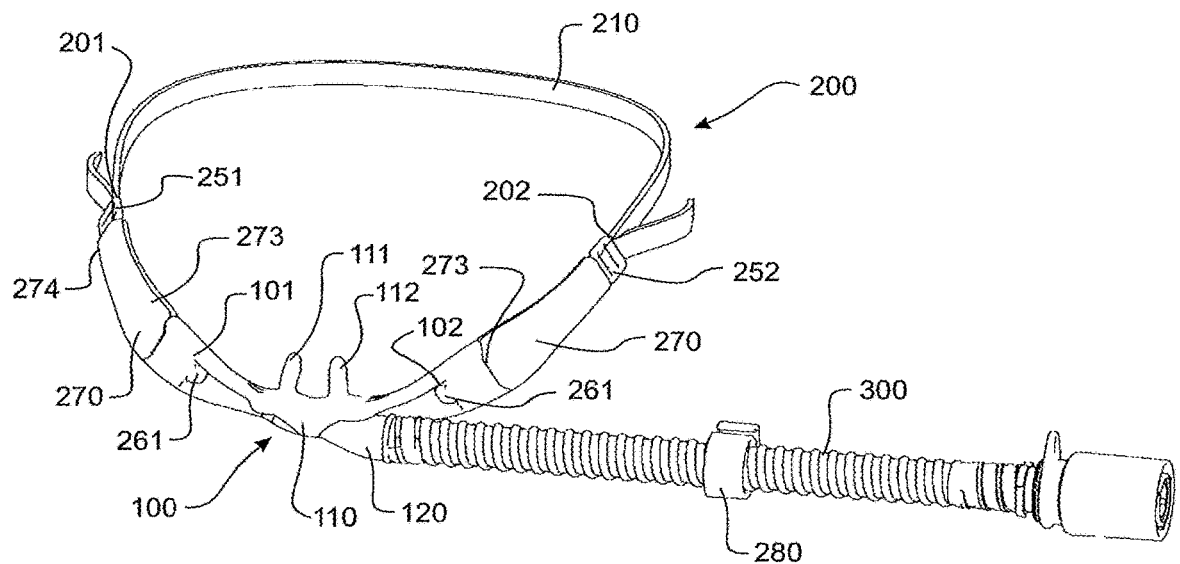
FIG. 4A is a perspective view of a preferred form patient interface and a third preferred form headgear of the invention in the assembled state.
Figure 4B:
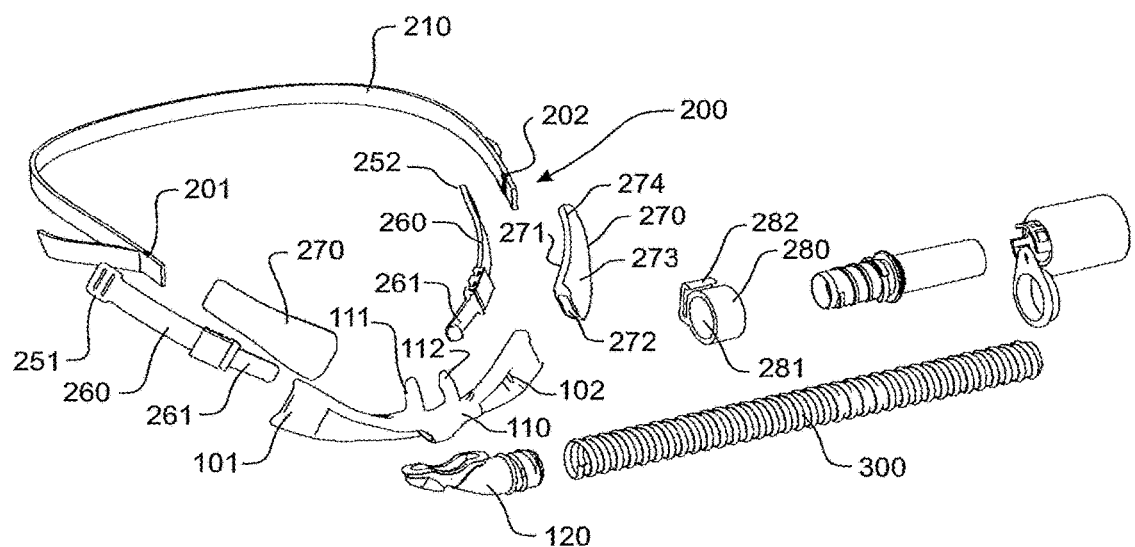
FIG. 4B is a perspective view of the patient interface and headgear of FIG. 4A in the disassembled state.
Figure 5:
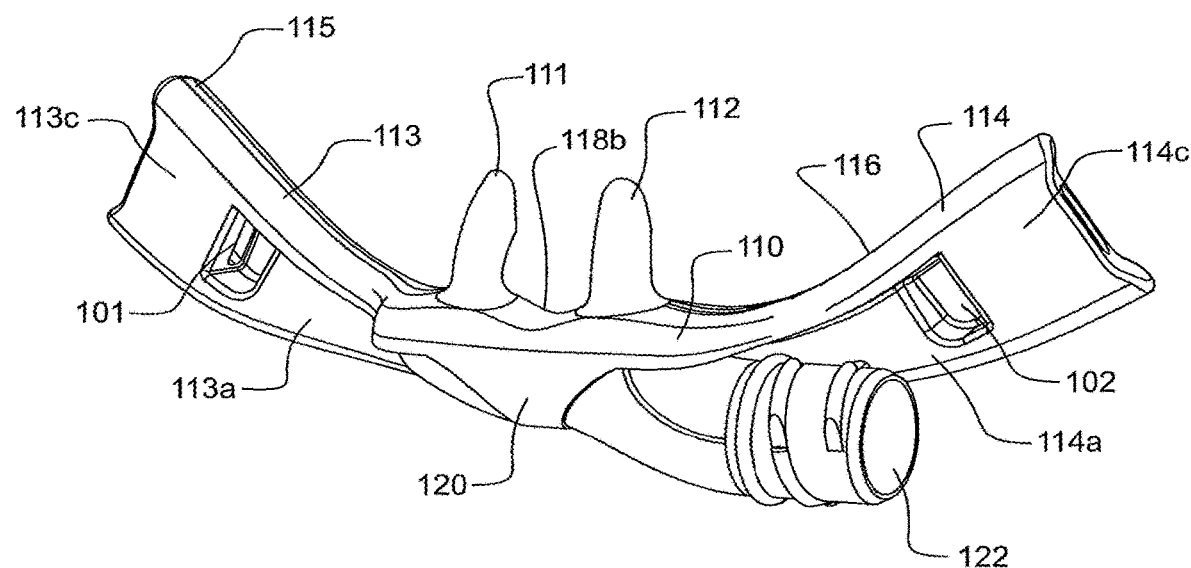
FIG. 5 is a perspective view of a face mount part of the preferred form patient interface of the invention from the outer side of the face mount part.
Figure 6:
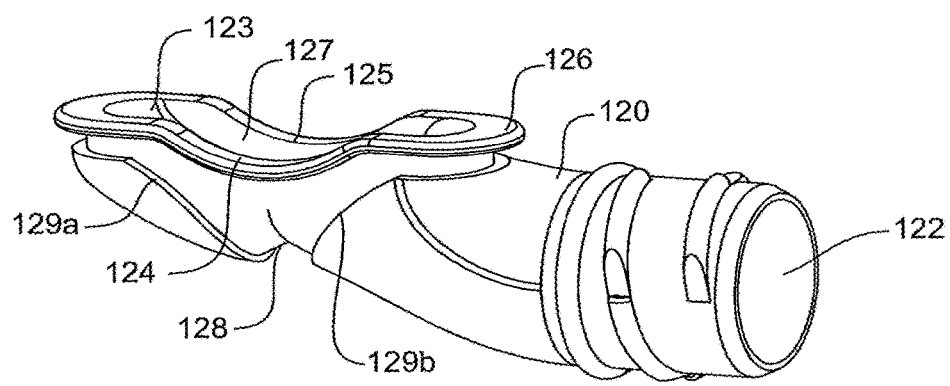
FIG. 6 is a perspective view of a gases flow manifold part of the preferred form patient interface of the invention.
Figure 7:
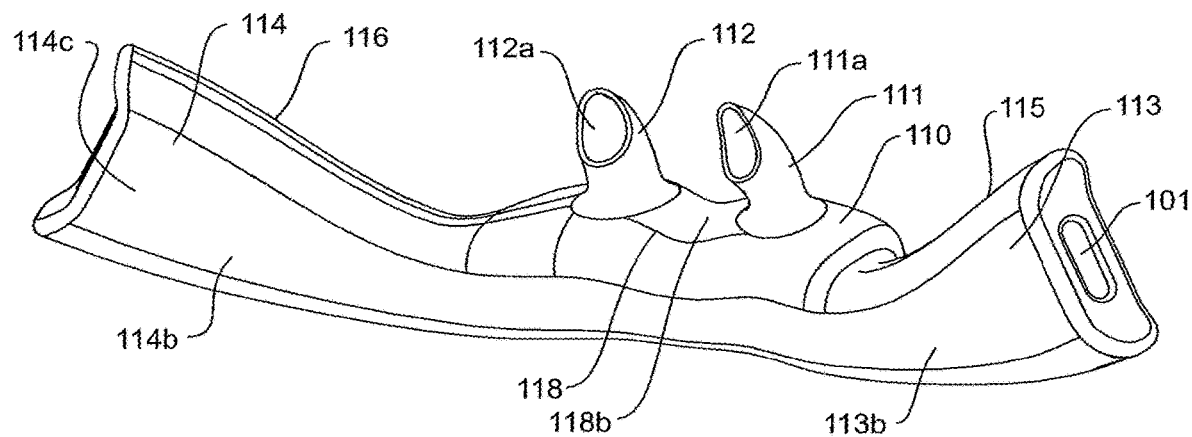
FIG. 7 is a perspective view of the face mount part of FIG. 5 from an inner side of the face mount part.
Figure 8:
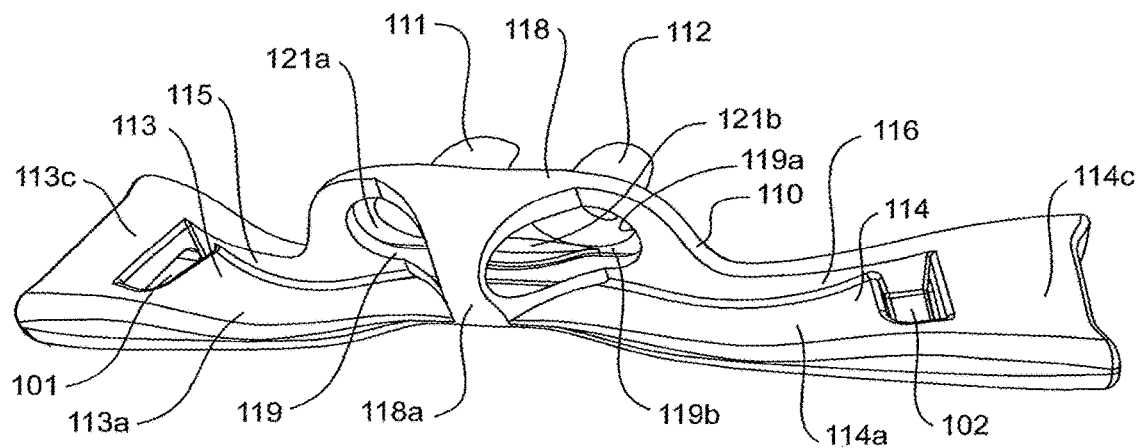
FIG. 8 is a perspective view of the face mount part of FIG. 5 from an underside of the face mount part.

Referring to FIGS. 4A and 4B, in the third preferred form adjustment mechanism a single strap is provided with the adjustment mechanism comprising two adjustment buckles 251 and 252 at the primary end portions 201 and 202 of the strap. The strap is looped about each adjustment buckle as is well known in the art and manipulated by the wearer on either side to adjust the effective length of the strap 210 in use. The side adjustment buckles 251 and 252 are located at or adjacent the cheeks of the wearer in use between ends 201 and 202 of the head strap 200 and the patient interface 100.

Figure 10:
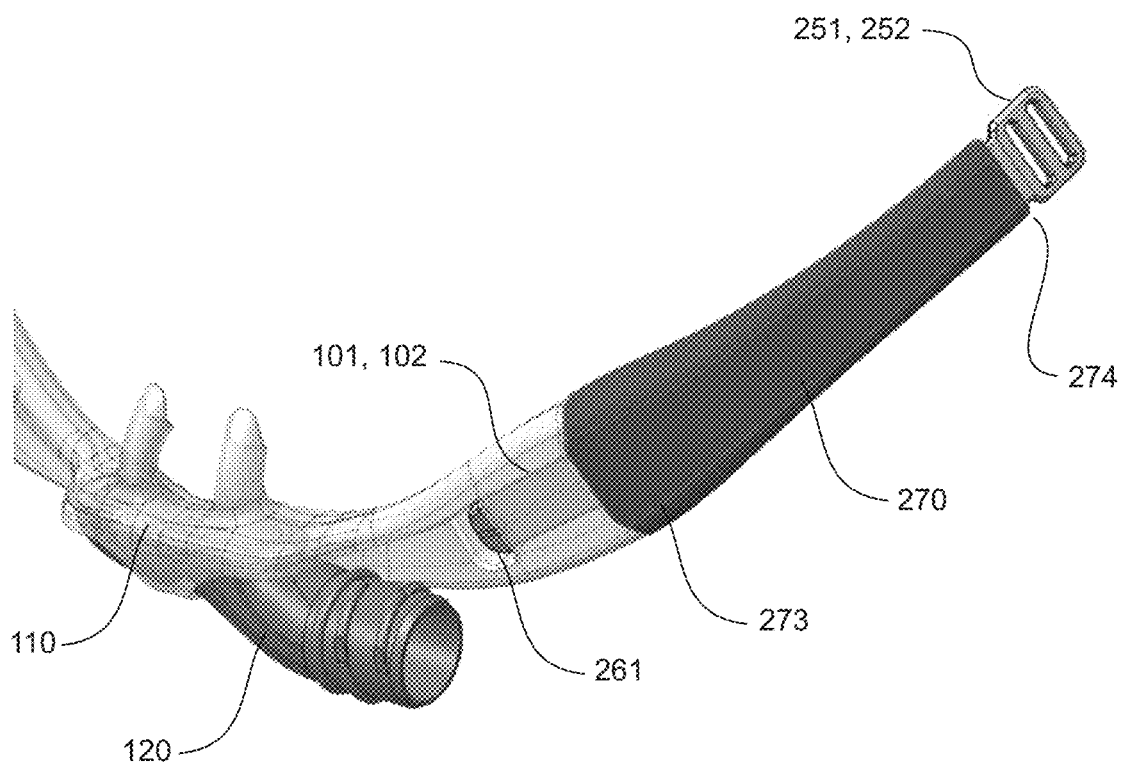
FIG. 10 is a close-up perspective view of the connection between the patient interface and the headgear of the FIG. 5 embodiment and showing a preferred form sleeve of the headgear.

Referring also to FIG. 10, in this embodiment the side buckles 251 and 252 are formed integrally with a cannula connector 260. The connector 260 comprises an elongate clip member, such as a push-fit clip 261 configured to releasably couple the respective formation 101/102 at the side of the cannula 110 at one end, and a strap buckle 251/252 at the opposing end. The clip 261 is elongate to extend in use, from the upper lip region of the patient to or at least substantially towards the patient's cheek. The clip member 261 is preferably a bendable part, such as a plastic part, that forms a hinged portion relative to the strap. The clip 261 is preferably preformed to have a curved shape along its length, such as one with an angle between flat and 20 degrees for example. The curve allows the clip 261 to fit the contour of the patient's face or cheek when the patient interface 100 and head strap 200 are appropriately worn by the patient.

Referring to FIGS. 14A-C and 15A-B, as in the first and second embodiments, the connector 260 comprises a clip member 261 having an elongate connector body 262 and a lateral projection 263 at a terminal end of the body 262. The lateral projection 263 comprises an inwardly facing engagement surface 263a. The face 264 of the connector 260 opposing the face 265 from which the projection 263 extends is preferably substantially smooth or planar. The corresponding formation 101/102 of the cannula 110 comprises a channel 101a/102a having entry 101b/102b and exit 101c/102c apertures at either end of the channel 101a/102a. A peripheral wall of the exit aperture 101c/102c defines an abutment 101ci/102ci configured to engage with the surface 263a of the projection 243 of the clip member 241. A periphery 101bi/102bi of the entry aperture 101b/102b defines an abutment for engaging a flange 266 at an opposing end of the body 262 to the projection 263. This acts to limit the extent of insertion of the connector 260 into the corresponding channel 101a/102a. The flange 266 may be provided by a terminal end of the strap connection mechanism and/or the sleeve 270.

The same method of insertion and/or removal of the connectors 260 into and/or from the cannula 110 as the one described above for the first headgear embodiment is applicable to this connector 260/embodiment as shown in FIGS. 14A-C and 15A-B.

It will be appreciated that for any one of the above head strap embodiments any other suitable connector configuration may be used to releasably connect the primary end portions of the strap to the nasal cannula.

Cheek Supports

Referring now to FIGS. 2-4, and 9 and 10, in the preferred embodiment, each section on either side of the head strap 200 and adjacent the respective primary end portion 201/202 includes or has applied thereto a cheek support 270 comprising at least a surface region 271 for frictionally engaging with the user's face to stabilise the headgear 200 on the face at the cheek, such as the cheekbone or below or a region thereof, both during coupling of the headgear to the patient interface 100 and after when in use. The surface region 270 is preferably of a relatively higher frictional surface material than the remainder of the strap 200.

The high friction surface material 271 is adapted to extend over a portion of the side of a patient's face in use, preferably at or at least substantially towards the patient's cheek, to assist with retaining or stabilising of the patient interface 100 upon the face of a patient. The high friction surface material, being locatable at the cheek of the user, further assists in keeping a remainder of the head strap 200 separated from and preferably extending below the eye or the orbit of the eye of the user, so as to prevent obstruction of vision and/or discomfort resulting from the head strap 200 bridging at or near the eye or eye orbit.

It will be appreciated the high friction surface material 271 may be adapted to extend over a portion of the side of a patient's face in use, for example, extending from at or near or above the left and right outer upper lips rearwardly and upwardly across the left and right cheeks.

In the preferred form the frictional surface material is provided in the form of an elongate sleeve 270 that is configured to receive the respective primary end portion 201/202 of the strap 200. The sleeve 270 is configured to removably couple (or alternatively be permanently coupled) about the strap 200, a section of the strap 200 and/or a cannula connector 240/260 at the primary end portion of the strap.

Referring to FIGS. 2, 3 and 9, in accordance with the first two preferred embodiments described above, the sleeve 270 is coupled about the strap 210 at the primary end portion 201/202 and also about a portion of the connector 240. The strap 210 extends through a passage 272 in the sleeve 270. The strap 210 is adapted to be threaded through this passage and preferably remains free to be stretched or elasticised or extended when in a sleeved configuration. The connector 240 is substantially housed by the sleeve 270 or shrouded by the surface region to minimise direct contact with the user's skin thereby improving stability comfort of the headgear 200. The clip 241 extends from an end 273 of the sleeve 270. In another embodiment, the sleeve 270 can be over-moulded on the connector 240 and/or the strap 210.

Referring to FIGS. 4 and 10, in accordance with the third preferred embodiment, the sleeve 270 is coupled about the connector 260 extending from the strap 210 at the primary end portion 201/202. In this embodiment the connector 260 is substantially housed by the sleeve 270 or shrouded by the surface region to minimise direct contact with the user's skin thereby improving stability and comfort of the headgear 200. In other words, the connector 260 extends fully though the passage 272 of the sleeve 270. The buckle 251/252 extends from an end 274 of the sleeve 270 and the clip 261 extends from the opposing end 273.

The sleeve 270 may be preformed to have a curved shape along its length, such as one with an angle between flat and 20 degrees for example. The curve allows the sleeve to fit the contour of the patient's face or cheek in the region of the sleeve in use. Alternatively the sleeve 270 may take on the shape of a curved sleeve upon engagement with the primary end portion 201/202 or connector 260 of the head strap 200.

The sleeve 270 provides a surface region of relatively higher frictional surface material for frictionally engaging with the user's face or facial skin. This surface region is to be positioned for frictional engagement with the facial cheek skin of a user. The surface region is at least localised to the strap or the section of strap which is to be positioned upon the cheeks of a user. The surface region provided with the relatively higher frictional surface material is preferably of a material that is smooth and comfortable on the skin of the patient. The sleeve 270 or at least the surface region 271 is therefore formed from a relatively softer material than the connectors 240 and 260.

In one preferred embodiment, the surface region 271 or the sleeve 270 is formed from a soft Thermoplastic Elastomer (TPE), but may alternatively be formed from another plastics material such as Silicone, or any other biocompatible materials.

The surface region 271 may be a surface of wider surface area more adjacent to the patient interface than the surface area more distant from the patient interface. In the preferred embodiment, the sleeve 270 tapers from a relatively wider surface area 273 to a relatively lesser surface area 274 in a direction extending away from a connection point between the connector 240/260 and the patient interface 100. The width of the sleeve at the end 273 is preferably the same or similar to the width of the tapered distal end 113c/114c of the corresponding wing portion 113/114 of the face mount part 110. This provides a smooth transition between the patient interface 100 and the headgear 200 for improving aesthetics and achieving a visually appealing effect.

Headgear for other forms of interface in addition to nasal cannula may comprise cheek supports 270 as described or similar, at or adjacent either side end of straps of headgear of the interface, which connect to the mask, for frictionally engaging with the user's face to stabilise the mask on the face at the cheeks, and particularly for example direct nasal masks comprising nozzles or pillows which enter or engage the nares of the wearer. Such headgear may again comprise a single head strap adapted to extend in use along the patient's cheeks, above the ears and about the back of the head, with ends comprising clips in any suitable form which couple to the mask on either side or are permanently attached to the mask.

Retention Clip

Figure 11B:
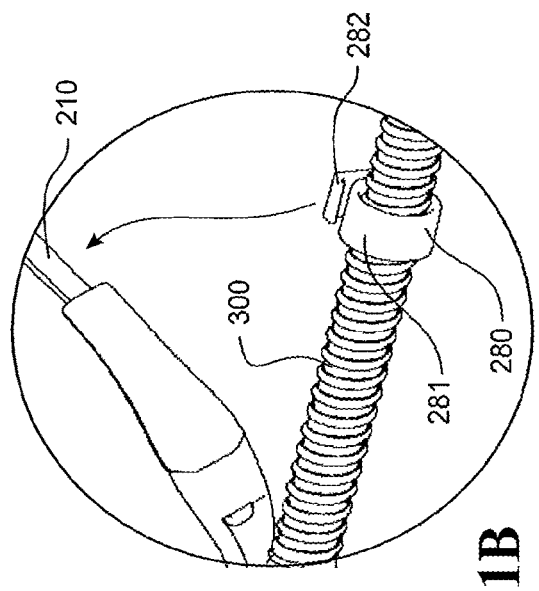
FIGS. 11A-11C show close up perspective views of a retention clip of the respiratory assistance system of the invention.
Figure 11C:
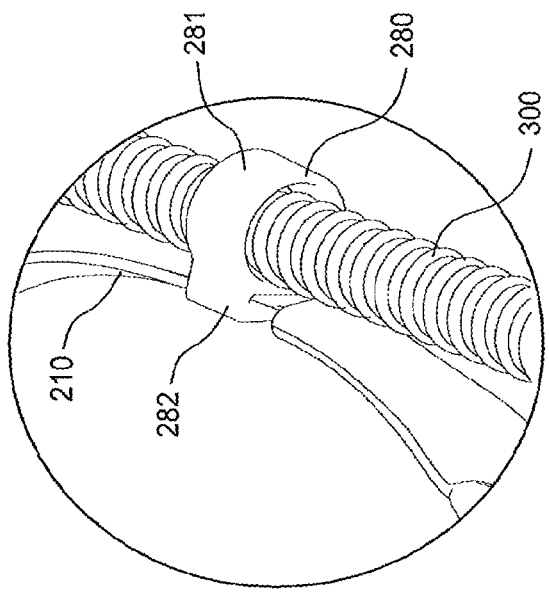
Figure 11A:
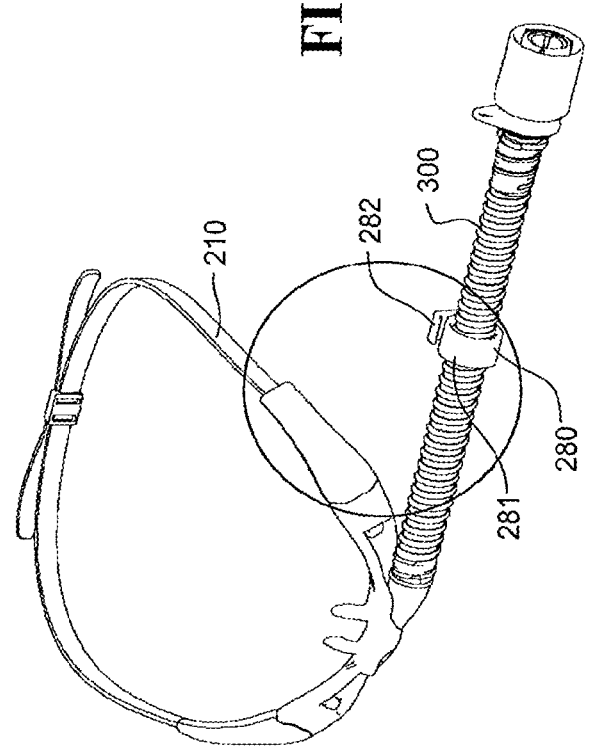

Referring to FIGS. 11A-11C, in the preferred embodiment a retention clip 280 is provided that comprises a tubular body 281 for receiving and accommodating a portion of the conduit 300 therein. A hook 282 projects from the body 281 to couple the strap or other component of the headgear 200. In this manner the conduit 300 can be coupled or tethered to the head strap 210 or headgear 200 in use. If the conduit 300 is pulled, the force will be exerted onto the head strap 210 and not directly on the cannula 100. This relocation of force will reduce the likelihood of the prongs 111 and 112 of the cannula 100 flicking out of the patient's nostrils.

One or more tethering points for connecting the clip 280 may be available on the headgear 200, with preferably at least two symmetric tethering points on either side of the headgear to increase usability.

It will also be appreciated the retention clip may be removeable from or may be a permanent fitting on the gas supply tube shown as item 300.

The retention clip 280 may be connected or retained to a part of the patient interface, such as for example a part of an interface which provides for a relatively more rigid region (such as to facilitate support of the gas supply tube item 300).

The retention clip may also be positioned or affixed at a particular location on the gas supply tube item 300, for example a predetermined location may be provided which holds the retention clip in place.

The conduit 300 may be a heated or an unheated conduit. The conduit may be an extension of any desired length.

Further Preferred Features

1. The cannula can have a generally low resistance to flow. In some configurations, the cannula can include tapering prongs. The taping prongs can close the nostrils for improved PEEP. The tapered nasal prongs would allow for less size options because a single design could be used for differently sized patients and can be fitted by vertical position within the nares of the user. For example, for patients with larger nares, the nasal prongs can be inserted deeper into the nares. In some configurations, the nasal prongs can flow expired air away from the patient to reduce heat.

2. Accentuated V-shape can help tip the prongs into the nose when the wings are pulled apart. In other words, the V-shape of the cheek pads and the stretching of the strap can pull the nasal prongs towards the patient and into the nares. The illustrated angles of the cheek pads can result in a construction that improves this aspect.

3. Dual fastening methods can be used so that the cannula generally can be held in place by a strap, or sticky pads (wiggle pads) or both of these together. The head strap can be adjustable from the back of the head, which is counter to most interface assemblies where adjustability is desired on the front to facilitate adjustment without reaching behind the head of the patient. The sticky pads can be positioned on the wings of the cannula. It is envisaged that younger children (e.g., less than 5 years old) will use the sticky pad plus the strap and the older children just the strap.

4. Large pads can fit on the cheek to reduce or eliminate pressure marks on the cheek. The pads can help stabilize the cannula on the face. The stabilization can reduce the likelihood or severity of roll out (e.g., twisting of the cannula). In some configurations, the cannula can include an overmolded piece or a structural piece to stiffen the base of the cannula while reducing the likelihood or severity of roll out.

In some configurations, the cannula can include a stabilizing ridge. In some such configurations, the stabilizing ridge can be positioned on the top of the cannula. In some such configurations, the stabilizing ridge on the top of the cannula can reduce or eliminate the likelihood of the prongs tipping out of the nose. The pads can have a soft surface on the under-side (i.e., the side that is adjacent to the face).

5. The pads can be mounted around the base of the prongs to reduce noise. The pad can be mounted at the base of the prongs. In some configurations, the pad can be a foam material. In some configurations, the pad can be a mouldable material that generally conforms to the patient's nose anatomy. In some configurations, soft cushions or pillows can be provided.

6. The surface around the base of the prongs can be contoured to reduce noise. In some configurations, the base of the prongs can include curved surfaces to provide for smoother airflow. The illustrated configuration, which is shown by drawings that are drawn to proportion, can provide a reduced noise level due to a smoother airflow.

7. The surface of the cannula that faces the user can include channels. The channels on the back of the cannula can facilitate or allow air to flow between the lip and the cannula to cool the patient.

Additional preferred feature combinations are now also defined according to the numbered paragraphs below:

1A. A strap as part of a headgear for a patient interface comprising:
  a strap, the strap having a pair of primary end portions, each of the primary end portions to be connected to a patient interface or to a component which is to be connected to the patient interface, and
  intermediate of each primary end portion is a pair of secondary end portions releasably connectable with each other to establish a continuous strap between the primary end portions of a starting length, the continuous strap for assisting in the retention of a patient interface upon a patient, and
  wherein each secondary end portion is adapted to be releasably connectable with a respective end portion of an additional strap segment to establish a continuous strap between the primary end portions of an extended strap length relative to the starting length.

2A. A strap as claimed in claim 1A wherein each end portion of the additional strap segment comprises a connector coupled to the strap segment and each secondary end portion of the strap comprises a connector coupled to the strap.

3A. A strap as claimed in claim 2A wherein the connector of each strap segment is configured to couple the connector the connector of the respective secondary end portion of the strap.

4A. A strap as claimed in either one of claim 1A or claim 2A wherein the connector of each secondary end portion of the strap is configured to couple the connector of the other secondary end portion of the strap and the connector of at least one end portion of the additional strap segment.

5A. A strap as claimed in any one of claim 2A to claim 4A wherein the connector of each of the end portion of the additional strap segment or the connector of each secondary end portion of the strap, or both, is of or comprises: male or female parts or both, for receipt by and connection to complementary male or female parts of another respective connector, and friction fit parts for retaining connection between the respective connectors.

6A. A strap as claimed in claim 5A wherein the connector comprises a projecting male part for receipt by a recessed female part of a respective connector and a recessed female part for receipt of a projecting male part of the respective connector.

7A. A strap as claimed in either claim 5A or claim 6A wherein the connector is capable of receiving and retaining a respective terminal end of the associated strap or associated additional strap segment.

8A. A strap as claimed in claim 7A wherein the connector is configured to retain the respective terminal end by a friction fit engagement.

9A. A strap as claimed in claim 8A wherein the connector comprises a series of internal teeth located upon a body of the connector for establishing a friction fit engagement with the respective terminal end, and a jaw of the body of the connector configured to close upon the teeth to securely retain the terminal end of the associated strap or associated additional strap segment upon the teeth.

10A. A strap as claimed in any one of the preceding claims wherein the strap is of an elastic, textile material.

11A. A strap as claimed in any one of the preceding claims wherein the additional strap segment is of an elastic, textile material.

12A. A strap as claimed in any one of the preceding claims wherein the additional strap segment comprises one or more additional strap segments releasably connectable to one another in an end to end relationship to formed a single continuous additional strap segment for releasably connecting to the secondary end portions of the strap.

13A. A strap as claimed in any one of the preceding claims wherein the additional strap segment is of any combination of one or more of the following lengths: about 2 cm, about 4 cm, or about 6 cm.

1B. A headgear for a patient interface comprising
a strap forming a part of the headgear for assisting in retaining or stabilising of a patient interface upon a user,
wherein the strap, or a section of the strap, to be located upon or to be placed in contact with the face or a portion of a user's face includes a surface region for frictionally engaging with the user's face, the surface region being of a relatively higher frictional surface material than the remainder of the strap forming the or a part of the headgear.

2B. A headgear as claimed in claim 1B wherein the strap or a respective section of the strap, includes two symmetric surface regions for frictionally engaging with two symmetric portions on either side of the user's face.

3B. A headgear as claimed in either one of claim 1B or claim 2B wherein a remainder of the strap is arranged to extend as a non-facial contacting strap or section of strap which is to extend beyond the user's face or the portion of the user's face.

4B. A headgear as claimed in any one of claim 1B or claim 3B wherein each surface region for frictionally engaging with the user's face or a portion of the user's face including the relatively higher frictional surface material assists with retaining or stabilising of a patient interface upon the face of a user.

5B. A headgear as claimed in any one of claim 1B to claim 4B wherein each surface region comprises a material applied to the strap or the respective section of strap.

6B. A headgear as claimed in claim 5B wherein the material applied is in the form of a sleeve positioned about the strap or the respective section of strap.

7B. A headgear as claimed in claim 6B wherein the sleeve is configured to removeably couple about the strap or the section of the strap.

8B. A headgear as claimed in claim 7B wherein the strap or the respective section of the strap extends through a passage in the sleeve.

9B. A headgear as claimed in claim 8B wherein the strap or the respective section of the strap is adapted to be threaded through the passage.

10B. A headgear as claimed in claim 5B wherein the material applied is in the form of a material coated upon the strap or the respective section of strap.

11B. A headgear as claimed in claim 5B wherein the material applied is over-moulded upon the strap or the respective section of strap. 12B. A headgear as claimed in any one of claim 4B to claim 11B wherein the material applied is smooth and comfortable for skin contact.

13B. A headgear as claimed in any one of claim 4B to claim 12B wherein the material applied is a Thermoplastic Elastomer.

14B. A headgear as claimed in any one of claim 1B to claim 13B wherein each surface region is a surface of wider surface area at an end to be located more adjacent to the patient interface than the surface area of an opposing end more distant from the patient interface.

15B. A headgear as claimed in claim 14B wherein each surface region tapers from the relatively wider surface area to the relatively lesser surface area.

16B. A headgear as claimed in any one of claim 1B to claim 15B wherein the strap or each section of the strap including the surface region further comprises a component of the strap configured to releasably couple the patient interface.

17B. A headgear as claimed in any one of claim 1B to claim 16B wherein each portion of the user's face includes a cheek of the user.

1C. A headgear for a patient interface comprising
a strap forming a part of the headgear for assisting in retaining or stabilising of a patient interface upon a user,
a first connector at a first end portion of the strap for connecting the strap to the patient interface, and
a first cheek engaging member adapted to encapsulate the first connector and having a surface region adapted to locate between the user's cheek and the connector to minimise direct contact of the connector with the user's skin in use.

2C. A headgear as claimed in claim 1C further comprising a second connector at a second opposing end portion of the strap for connecting the strap to the patient interface, and a second cheek engaging member configured to encapsulate the second connector and having a surface region adapted to locate between the user's other cheek to minimise direct contact of the connector with the user's skin in use.

3C. A headgear as claimed in either one of claim 1C or claim 2C wherein each cheek engaging member is configured to removeably couple about the respective connector.

4C. A headgear as claimed in any one of claim 1C to claim 3C wherein the surface region of each cheek engaging member comprises a material that is substantially softer than a material of the respective connector.

5C. A headgear as claimed in any one of claim 1C to claim 4C wherein the surface region of each cheek engaging member comprises of a relatively higher frictional surface material than the respective connector to assist with retaining or stabilising of a patient interface upon the face of a user.

6C. A headgear as claimed in either claim 4C or claim 5C wherein the material is a Thermoplastic Elastomer.

7C. A headgear as claimed in any one of claim 1C to claim 6C the surface region of each cheek engaging member is a surface of wider surface area at an end of the respective cheek engaging member more adjacent to the patient interface than a surface area of an opposing end of the cheek member more distant from the patient interface.

8C. A headgear as claimed in claim 8C wherein the surface region of each cheek engaging members tapers from a relatively wider end to a relatively lesser end.

9C. A headgear as claimed in any one of claim 1C to 8C wherein each cheek engaging member is a sleeve configured to receivably retain the respective connector therein.

10C. A headgear as claimed in claim 9C wherein the sleeve is configured to removably couple about the respective connector.

11C. A headgear as claimed in either one of claim 9C or claim 10C wherein the connector is adapted to extend through a passage in the sleeve.

12C. A headgear as claimed in any one of claim 9C to claim 11C wherein each connector is substantially housed by the respective sleeve in a region adapted to locate adjacent the user's cheek in use.

13C. A headgear as claimed in any one of claim 9C to claim 12C wherein each sleeve is curved along at least a portion of the length of the sleeve to complement the contour of the respective cheek.

14C. A headgear as claimed in any one of claim 9C to claim 13C wherein each connector is curved along at least a portion of the length of the connector adapted to locate adjacent the respective cheek.

15C. A headgear as claimed in claim 14C wherein the connector is preformed with a curved profile.

16C. A headgear as claimed in any one of claim 13C to claim 15C wherein each sleeve is preformed with a curved profile.

17C. A headgear as claimed in any one of claim 13C to claim 15C wherein each sleeve is curved upon encapsulating the respective connector.

18C. A headgear as claimed in any one of claim 1C to claim 17C wherein the connector comprises a clip for releasably connecting with the patient interface.

19C. A headgear as claimed in any one of claim 1C to claim 18C wherein each connector is frictionally or mechanically engaged with the respective cheek engaging member once in-situ.

1D. A nasal cannula comprising:
  a face mount part having a base portion and at least one elongate wing portion extending laterally from a side of the base,
  at least one nasal prong extending transversely from the base portion and capable of fitting in at least one of a user's nares, and
  wherein each wing portion comprises an exterior surface adapted to contact a portion of a user's face in use, and an elongate ridge extending transversely along the wing portion from a side of the wing portion opposing the exterior surface to aid in stabilising the face mount part upon the user's face in use.

2D. A nasal cannula as claimed in claim 1D wherein the face mount part comprises a pair of wing portions extending laterally from either side of the base.

3D. A nasal cannula as claimed in either claim 1D or claim 2D wherein the face mount part comprises a pair of nasal prongs for fitting in each of the user's nares.

4D. A nasal cannula as claimed in any one of claim 1D to claim 3D wherein the elongate ridge of each wing portion extends along an upper region of the wing portion.

5D. A nasal cannula as claimed in any one of claim 1D to claim 4D wherein each wing portion comprises an accentuated terminal end extending in a direction substantially towards the user's respective cheek in use.

6D. A nasal cannula as claimed in claim 5D wherein the terminal end of each wing portion is angled obtusely relative to a longitudinal orientation of the base portion.

7D. A nasal cannula as claimed in either one of claims 6D or claim 7D wherein the terminal end of each wing portion is of a substantially greater contact surface area than a contact surface area of the wing portion adjacent the base portion.

8D. A nasal cannula as claimed in claim 7D wherein the terminal end of each wing portion tapers outwardly.

9D. A nasal cannula as claimed in any one of claim 1D to claim 8D wherein a distal end of each wing portion comprises a formation configured to releasably couple a complementary connector of a headgear associated with the cannula.

10D. A nasal cannula as claimed in any one of claim 1D to claim 9D further comprising a bridge extending from the base portion to a lower region of the wing portion and forming a side entry on either side of the bridge.

11D. A nasal cannula as claimed in claim 10D further comprising a gases flow manifold part having a gases inlet for receiving a flow of gas from a gas source, and a gases outlet for delivering the flow of gas to the at least one nasal prong of the face mount part, the manifold part being adapted to be received by the base portion through either side entry of the face mount part to fluidly connect the outlet of the manifold with the nasal prongs of the face mount part.

12D. A nasal cannula as claimed in claim 11D wherein the face mount part further comprises a recess formed in an interior of the base portion, and the gases flow manifold part comprises a corresponding lip at the outlet adapted to releasably engage the recess to fluidly connect the outlet with the nasal prongs of the face mount part.

1E. A nasal cannula assembly comprising:
  a face mount part having a base portion and at least one nasal prong extending from the base portion and capable of fitting in at least one of a user's nares, and
  a gases flow manifold part having a gases inlet for receiving a flow of gas from a gas source, and a gases outlet for delivering the flow of gas to the at least one nasal prong of the face mount part, the manifold part being adapted to be received by the base portion of the face mount part to fluidly connect the outlet of the manifold with the at least one nasal prong of the face mount part, and wherein the manifold part further comprises a groove at the outlet to establish a gap between the base portion of the face mount part and the manifold part in a region of the base portion configured to locate adjacent a user's philtrum in use to thereby eliminate or at least alleviate pressure on the user's septum from the manifold part in use.

2E. A nasal cannula as claimed in claim 1E wherein the gases flow manifold part is formed from a relatively harder material than the face mount part.

3E. A nasal cannula as claimed in either claim 1E or claim 2E wherein the gases flow manifold part is formed from a substantially rigid plastics material, such as Polycarbonate.

4E. A nasal cannula as claimed in any one of claim 1E to claim 3E wherein the face mount part is formed from a substantially soft plastics material, such as Silicone.

5E. A nasal cannula as claimed in any one of claim 1E to claim 4E wherein the groove at the outlet of the manifold part is formed by a pair of opposed recesses on either side of a periphery of the outlet.

6E. A nasal cannula as claimed in claim 5E wherein the periphery of the outlet of the manifold is adapted to sealably engage an interior of the base portion of the face mount part.

7E. A nasal cannula as claimed in claim 6E, wherein the outlet of the manifold part comprises a lip extending about the periphery of the outlet and the interior of the base portion comprises a corresponding recess adapted to releasably receive the lip of the outlet of the manifold part.

8E. A nasal cannula as claimed in any one of claim 1E to claim 7E wherein the face mount part comprises at least one substantially horizontal side entry passage to the interior of the base portion for releasably receiving the outlet of the manifold part therethrough.

9E. A nasal cannula as claimed in claim 8E wherein the face mount part comprises a pair of opposed side entry passages to the interior of the base portion, each adapted to releasably receive the outlet of the manifold part therethrough.

10E. A nasal cannula as claimed in any one of claim 1E to claim 9E wherein the face mount part comprises a pair of nasal prongs.

11E. A nasal cannula as claimed in claim 10E wherein the base portion of the face mount part comprises a dipped region between the nasal prongs to extend the base portion away from the user's septum and further alleviate pressure on the septum in use.

1F. A patient interface comprising a nasal cannula as claimed in any one of claim 1D to claim 12D, or any one of claim 1E to claim 11E or any combination thereof.

2F. A headgear as claimed in any one of claim 1A to claim 13A, or claim 1B to claim 17B, or claim 1C to claim 19C, or any combination thereof.

3F. A headgear as claimed in claim 2F further comprising a head band adapted to extend over the user's crown.

4F. A headgear as claimed in either one of claim 1F or claim 2F wherein a strap of the headgear is formed from an elastic material.

5F. A headgear as claimed in any one of claim 2F to claim 4F wherein a strap of the headgear is formed from a textile material.

6F. A respiratory assistance system comprising:
a patient interface as claimed in claim 1F for delivering a flow of humidified gas to a patient, and
a headgear as claimed in any one of claim 2F to claim 5F for retaining the patient interface upon the patient's face.

7F. A respiratory assistance system as claimed in claim 6F further comprising a ventilator adapted to generate a flow of gases, and a humidifier coupled to the outlet of the ventilator for humidifying the flow of gases.

8F. A respiratory assistance system as claimed in claim 7F further comprising an inspiratory conduit adapted to couple between the humidifier and the patient interface.

9F. A respiratory assistance system as claimed in claim 8F further comprising an extension tube adapted to couple between the inspiratory conduit and the patient interface.

10F. A respiratory assistance system as claimed in claim 9F further comprising a retention clip adapted to couple about the extension tube and to the headgear to thereby tether the tube to the headgear and relocate at least a portion of a pull force on the extension tube from by the patient interface to the headgear.

1G. A method of disconnecting a headgear comprising at least one connector at a terminal end of the headgear from a patient interface comprising an elastically deformable formation for receiving and retaining the connector, the method comprising the steps of:
rotating the connector axially within the formation to alter the orientation of the connector, and
pulling the connector away from the formation to disengage the connector from the patient interface.

2G. A method as claimed in claim 1G wherein the step of rotating the connector comprises rotating the connector axially approximately 180 degrees.

3G. A method as claimed in either claim 1G or claim 2G wherein the connector comprises an elongate body and a lateral projection extending from the body, and the corresponding formation of the patient interface comprises a channel having an entry aperture and an exit aperture and an abutment surface at a periphery of the exit aperture, and wherein the step of rotating the connector axially comprises rotating the connector to disengage the projection from the abutment surface, and the step of pulling the connector comprises pulling the connector through the channel and out of the entry aperture.

4G. A method as claimed in any one of claim 1G to claim 3G wherein the headgear comprises a connector at either end of the headgear, and the patient interface comprises a corresponding formation at either side of the interface.

The foregoing description of the invention includes preferred forms thereof. Modifications may be made thereto without departing from the scope of the invention as defined by the accompanying claims.

The invention claimed is:

1. A headgear for a patient interface comprising:
a strap forming a part of the headgear configured to assist with retaining or stabilizing the patient interface upon a face of a user,
wherein the strap, or a section of the strap, configured to be located upon or to be placed in contact with the face of the user or a portion of the face of the user comprises a surface region configured for frictionally engaging with the face of the user,
wherein the surface region comprises a relatively higher frictional surface material than a remainder of the strap,
wherein a sleeve is positioned about the strap or the section of the strap, the sleeve comprising the relatively higher frictional surface material.

2. The headgear of claim 1, wherein the strap comprises two symmetric surface regions configured for frictionally engaging with the face of the user.

3. The headgear of claim 2, wherein each surface region is configured to assist with retaining or stabilizing the patient interface upon the face of the user.

4. The headgear of claim 1, wherein the remainder of the strap is configured to extend as a non-facial contacting strap or a non-facial contacting section of strap beyond the face of the user or the portion of the face of the user.

5. The headgear of claim 1, wherein the surface region comprises a material applied to the strap or the section of strap.

6. The headgear of claim 1, wherein the sleeve is configured to removably couple with the strap or the section of the strap.

7. The headgear of claim 1, wherein the strap or the section of the strap extends through a passage in the sleeve.

8. The headgear of claim 1, wherein the strap or the section of the strap is configured to be threaded through a passage in the sleeve.

9. The headgear of claim 1, wherein the relatively higher frictional surface material is coated or over-moulded upon the strap or the section of strap.

10. The headgear of claim 1, wherein the relatively higher frictional surface material is smooth.

11. The headgear of claim 1, wherein the relatively higher frictional surface material is a thermoplastic elastomer.

12. The headgear of claim 1, wherein the surface region comprises a wider surface area at an end closer to the patient interface than a surface area of an opposing end farther from the patient interface.

13. The headgear of claim 1, wherein the surface region tapers from a relatively wider surface area to a relatively lesser surface area.

14. The headgear of claim 1, wherein the strap or the section of the strap comprises a component configured to releasably couple with the patient interface.

15. The headgear of claim 1, wherein the surface region is configured for frictionally engaging with a cheek of the user.

16. A patient interface comprising:
a nasal cannula; and
the headgear of claim 1.

17. The patient interface of claim 16, wherein the nasal cannula comprises a face mount part comprising a pair of wing portions extending laterally from either side of a base portion.

18. The patient interface of claim 17, wherein a distal end of each wing portion is formed with a substantially greater contact surface area than a contact surface area of each wing portion in a region nearest a pair of nasal prongs.

19. The patient interface of claim 17, wherein the pair of wing portions are angled relative to a longitudinal axis of the face mount part or the base portion, and wherein the pair of wing portions extend obtusely away from the base portion.

20. The patient interface of claim 17, wherein a ridge extends along an upper region of each wing portion.

21. The patient interface of claim 17, further comprising a gases flow manifold part configured to be inserted into the face mount part from either a left side or a right side such that the manifold part is reversible.

22. A headgear for a patient interface comprising:
a strap forming a part of the headgear for assisting in retaining or stabilizing of a patient interface upon a user,
wherein the strap, or a section of the strap, to be located upon or to be placed in contact with a face or a portion of a face of a user includes a surface region for frictionally engaging with the face of the user, the surface region being of a relatively higher frictional surface material than a remainder of the strap forming the headgear or a part of the headgear,
wherein the surface region is a surface of a wider surface area more adjacent to the patient interface than a surface area more distant from the patient interface,
wherein the surface region comprises a material applied to the strap, or the section of strap, the material applied as a sleeve positioned about the strap, or the section of strap, and
wherein the surface region tapers from the surface of the wider surface area at an end to be located more adjacent to the patient interface, to a relatively lesser surface area at an opposing end more distant from the patient interface.

23. The headgear of claim 22, wherein the strap or a section of the strap, includes two symmetric surface regions for frictionally engaging with two symmetric portions on either side of the face of the user.

24. The headgear of claim 23, wherein a remainder of the strap is arranged to extend as a non-facial contacting strap or section of strap which is to extend beyond the face of the user or the portion of the face of the user.

25. The headgear of claim 22, wherein each surface region for frictionally engaging with the face of the user or a portion of the face of the user, including the surface region that is of the relatively higher frictional surface material, assists with retaining or stabilizing of a patient interface upon the face of the user.

26. The headgear of claim 22, wherein the sleeve is configured to removably couple about the strap or the section of the strap.

27. The headgear of claim 26, wherein the strap or the section of the strap extends through a passage in the sleeve.

28. The headgear of claim 27, wherein the strap or the section of the strap is adapted to be threaded through the passage.

29. The headgear of claim 28, wherein the strap remains free to be stretched or elasticized or extended when in a sleeved configuration.

30. The headgear of claim 22, wherein the material applied is a material coated upon the strap or the section of the strap.

31. The headgear of claim 22, wherein the material applied is over-moulded upon the strap or the section of the strap.

32. The headgear of claim 31, wherein the material applied is smooth and comfortable for skin contact.

33. The headgear of claim 32, wherein the material applied is a Thermoplastic Elastomer.

34. The headgear of claim 22, wherein the strap or section of the strap including the surface region further comprises a component of the strap configured to releasably couple the patient interface.

35. The headgear of claim 22, wherein a width of the surface of the wider surface area at the end located more adjacent to the patient interface is similar to a width of a portion of the patient interface to which the strap couples.

36. The headgear of claim 22 further comprising a connector, wherein the sleeve is configured to receiveably retain the connector.

37. The headgear of claim 36, wherein the sleeve is configured to removably couple about the connector.

38. The headgear of claim 37, wherein the connector comprises a first male connection part, and the sleeve comprises a corresponding second female connection part to couple the sleeve and the connector.

39. The headgear of claim 36, wherein the connector is adapted to extend through a passage in the sleeve.

40. The headgear of claim 39, wherein the connector is substantially housed by the sleeve in a region adapted to located adjacent a cheek of the face of the user in use.

41. The headgear of claim 40, wherein each portion of the face of the user includes a cheek of the user.

42. The headgear of claim 22 further comprising a patient interface comprising a nasal cannula assembly and the headgear.

43. The headgear of claim 42, wherein the nasal cannula assembly comprises:
a face mount part having a base portion and at least one nasal prong extending from the base portion and capable of fitting in at least one of nares of the user; and
a gases flow manifold part having a gases inlet for receiving a flow of gas from a gas source, and a gases outlet for delivering the flow of gas to the at least one nasal prong of the face mount part, the gases flow manifold part adapted to be received by the base portion of the face mount part to fluidly connect the gases outlet of the gases flow manifold part with the at least one nasal prong of the face mount part, and wherein the gases flow manifold part further comprises a groove at the gases outlet to establish a gap between the base portion configured to locate adjacent a philtrum of a user in user to eliminate or at least alleviate pressure on a septum of the user from the gases flow manifold part in use.

44. The headgear of claim 43, wherein the face mount part comprises at least one elongate wing portion extending laterally from a side of the base portion, and wherein a width of the sleeve is of a substantially similar width to the at least one elongate wing portion.

45. A headgear for a patient interface comprising:
a strap forming a part of the headgear, the strap assisting in retaining the patient interface upon a user,
wherein two sections of the strap configured to be located upon a portion of a face of the user on either side of the patient interface each include a respective surface region for frictionally engaging with the face of the user, the respective surface regions being of a relatively higher frictional surface material than a remainder of the strap, the relatively higher frictional surface material of the respective surface regions configured to assist with retaining the patient interface upon the face of the user,
wherein each of the respective surface regions comprises a material applied to a respective section of the strap, the material applied as a sleeve positioned about the respective section of the strap,
wherein each of the respective surface regions is a surface of wider surface area at an end of the respective surface regions to be located more adjacent to the patient interface than a surface area of an opposing end of the respective surface regions more distant from the patient interface, and
wherein each of the respective surface regions tapers from the surface of wider surface area to the surface area of the opposing end.

46. The headgear of claim 45, wherein the two sections of the strap include at least two symmetric surface regions, the at least two symmetric surface regions for frictionally engaging with two symmetric portions on either side of the face of the user.

47. The headgear of claim 45, wherein a remainder of the strap is arranged to extend as a non-facial contacting section of strap which is to extend beyond the portion of the face of the user.

48. The headgear of claim 45, wherein the sleeve is configured to removably couple about the respective section of the strap.

49. The headgear of claim 48, wherein the respective section of the strap extends through a passage in the sleeve or wherein the respective section of the strap is adapted to be threaded through the passage in the sleeve.

50. The headgear of claim 49, wherein the strap remained free to be stretched or elasticized or extended when in a sleeved configuration.

51. The headgear of claim 45, wherein the material applied is smooth and comfortable for skin contact.

52. The headgear of claim 45, wherein the material applied is a Thermoplastic Elastomer.

53. The headgear of claim 45, wherein the strap further comprises a component configured to releasably couple the patient interface.

54. The headgear of claim 45, wherein a width of the surface of wider surface region at the end of the respective surface regions is similar to a width of a tapered distal end of a wing portion of the patient interface to which the strap couples.

55. The headgear of claim 45 further comprising a connector, wherein the sleeve is configured to receiveably retain the connector therein, optionally wherein the sleeve is configured to removably couple about the connector, and optionally wherein the connector comprises a first male connection part, and the sleeve comprises a corresponding second female connection part to couple the sleeve and connector.

56. The headgear of claim 55, wherein the connector is adapted to extend through a passage in the sleeve, optionally wherein the connector is substantially housed by the sleeve in a region adapted to locate adjacent a cheek of the user in use.

57. The headgear of claim 45, wherein the portion of the face of the user upon which one of the two sections of the strap is to be located includes a cheek of the user.

* * * * *